(12) United States Patent
Paulini et al.

(10) Patent No.: US 8,252,939 B2
(45) Date of Patent: Aug. 28, 2012

(54) SULFOXIMINAMIDE COMPOUNDS FOR COMBATING ANIMAL PESTS

(75) Inventors: Ralph Paulini, Bad Dürkheim (DE); Delphine Breuninger, Bobenheim-Roxheim (DE); Wolfgang von Deyn, Neustadt (DE); Henricus Maria Martinus Bastiaans, Usingen (DE); Carsten Beyer, Mainz (DE); Douglas D. Anspaugh, Apex, NC (US); Hassan Oloumi-Sadeghi, Raleigh, NC (US); Faraneh Oloumi, legal representative, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/000,814

(22) PCT Filed: Jun. 19, 2009

(86) PCT No.: PCT/EP2009/057650
§ 371 (c)(1),
(2), (4) Date: Aug. 4, 2011

(87) PCT Pub. No.: WO2009/156336
PCT Pub. Date: Dec. 30, 2009

(65) Prior Publication Data
US 2011/0306493 A1 Dec. 15, 2011

Related U.S. Application Data

(60) Provisional application No. 61/074,822, filed on Jun. 23, 2008.

(51) Int. Cl.
*A01N 43/64* (2006.01)
*C07D 213/00* (2006.01)
(52) U.S. Cl. ........................... 546/329; 514/357
(58) Field of Classification Search .......... None
See application file for complete search history.

(56) References Cited

U.S. PATENT DOCUMENTS

| 2008/0108666 A1 | 5/2008 | Loso et al. |
| 2008/0108667 A1 | 5/2008 | Zhu et al. |

FOREIGN PATENT DOCUMENTS

| EP | 173498 | 3/1986 |
| GB | 1307271 | 2/1973 |
| WO | WO 96/39389 | 12/1996 |
| WO | WO 2006037945 | 4/2006 |
| WO | WO 2006060029 | 6/2006 |
| WO | WO 2008030266 | 3/2008 |

OTHER PUBLICATIONS

International Search Report, issued in PCT/EP2009/057650, dated Sep. 14, 2009.
International Preliminary Report on Patentability, issued in PCT/EP2009/057650, dated Jan. 13, 2011.

*Primary Examiner* — Janet Andres
*Assistant Examiner* — Heidi Reese
(74) *Attorney, Agent, or Firm* — Brinks Hofer Gilson & Lione

(57) ABSTRACT

The invention relates to sulfoximinamid compounds of formula (I), to the enantiomers, diastereomers and salts thereof and to compositions comprising such compounds. The invention also relates to the use of the sulfoximinamid compounds, of their salts or of compositions comprising them for combating animal pests. Furthermore the invention relates also to methods of applying such sulfoximine compounds. The sulfoximinamid compounds of the present invention are defined by the following formula I: wherein Q, Het, $R^1$, $R^2$, $R^3$, $R^4$ and n are defined as in the description.

formula (I)

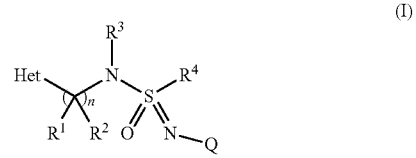

24 Claims, No Drawings

SULFOXIMINAMIDE COMPOUNDS FOR COMBATING ANIMAL PESTS

This application is a National Stage application of International Application No. PCT/EP2009/057650, filed Jun. 19, 2009, which claims the benefit of U.S. Provisional Application No. 61/074,822, filed Jun. 23, 2008, the entire contents of which are hereby incorporated herein by reference.

The present invention relates to sulfoximinamid compounds, to the enantiomers, diastereomers and salts thereof and to compositions comprising such compounds. The invention also relates to the use of the sulfoximinamid compounds, of their salts or of compositions comprising them for combating animal pests. Furthermore the invention relates also to methods of applying such compounds.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

It is therefore an object of the present invention to provide compounds having a good pesticidal activity, especially against difficult to control insects and acaridae.

It has been found that these objects are solved by sulfoximinamid derivatives of the general formula I:

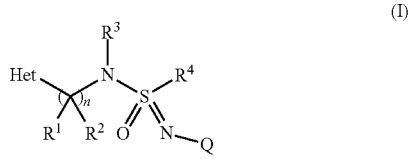

(I)

wherein

Q is $NO_2$ or CN;

n is 0, 1 or 2;

$R^1$ and $R^2$ are selected independently from one another and independently from n from hydrogen, halogen, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, CN, $NO_2$, $C(O)R^c$, $C(O)OR^a$, $C(O)NR^aR^b$, $C(S)NR^aR^b$ or $S(O)_mR^c$, and wherein the carbon atoms in the aforementioned groups may carry any combination of 1, 2 or 3 radicals $R^d$;

or $R^1$ and $R^2$ form together with the carbon atom, which they attached to, a 3- to 6-membered carbocyclic ring, and wherein the carbon atoms of the ring may carry any combination of 1 or 2 radicals $R^d$;

$R^3$ is selected from hydrogen, $C_1$-$C_6$-alkyl, $C_3$-$C_6$-cycloalkyl, $C_1$-$C_6$-alkoxy, $C_2$-$C_6$-alkenyl, $C_2$-$C_6$-alkynyl, $C(O)R^c$, $C(O)OR^a$, $C(O)NR^aR^b$, $C(S)NR^aR^b$, $SO_mR^c$ or $NR^e$, and wherein the carbon atoms in the aforementioned groups may carry any combination of 1, 2 or 3 radicals $R^d$;

$R^4$ is selected from $C_1$-$C_6$-alkyl, $C_3$-$C_6$-cycloalkyl, $C_2$-$C_6$-alkenyl, $C_2$-$C_6$-alkynyl or $NR^eR^f$, and wherein the carbon atoms in the aforementioned groups may carry any combination of 1, 2 or 3 radicals $R^d$;

or $R^3$ and $R^4$ form together with the nitrogen and sulfur atom they are bond to a saturated or unsaturated 4-, 5- or 6-membered heterocyclic ring, optionally containing an additional heteroatom selected from N, O, S, whereas the carbon atoms of the heterocyclic ring may optionally carry any combination of 1 or 2 radicals $R^d$ and whereas the additional N atom optionally may carry $R^e$;

Het is selected from

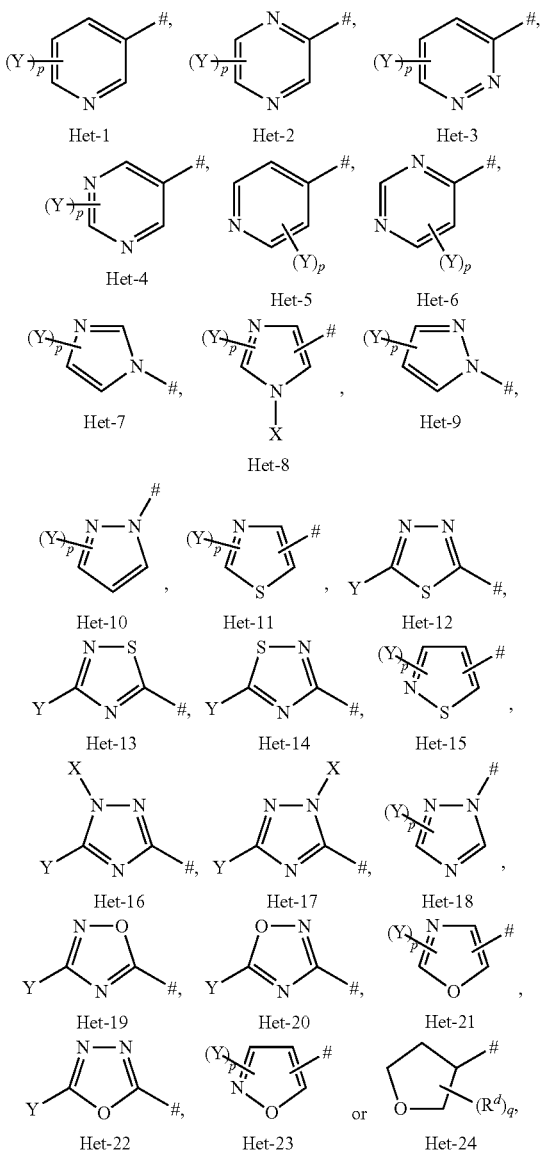

wherein # denotes the bond in formula (I), and

X is selected from hydrogen, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C(O)R^c$, $C(O)OR^5$, $C(O)NR^aR^b$, $C(S)NR^aR^b$ or $S(O)_mR^c$, and wherein the carbon atoms in the aforementioned groups may carry any combination of 1, 2 or 3 radicals $R^d$;

Y is selected from halogen, $C_1$-$C_6$ alkyl, $C_3$-$C_6$ cycloalkyl, $C_2$-$C_6$ alkenyl, $C_2$-$C_6$ alkynyl, $C_1$-$C_6$ alkoxy, CN, $NO_2$, $S(O)_mR^c$, $C(O)R^c$, $C(O)OR^a$, $C(O)NR^aR^b$ or $C(S)NR^aR^b$, and wherein the carbon atoms in the aforementioned groups may carry any combination of 1, 2 or 3 radicals $R^d$;

p is 0, 1 or 2;

q is 0, 1 or 2;

and wherein
R$^a$, R$^b$ are selected independently from one another from hydrogen, C$_1$-C$_4$-alkyl, C$_1$-C$_4$-haloalkyl, C$_3$-C$_6$-cycloalkyl, C$_3$-C$_6$-alkenyl, C$_3$-C$_6$-haloalkenyl or C$_3$-C$_6$-alkynyl;

R$^c$ is selected from C$_1$-C$_4$-alkyl, C$_1$-C$_4$-haloalkyl, C$_3$-C$_6$-cycloalkyl, C$_2$-C$_6$-alkenyl, C$_2$-C$_6$-haloalkenyl or C$_2$-C$_6$-alkynyl;

R$^d$ is selected from halogen, C$_1$-C$_4$-alkyl, C$_1$-C$_4$-haloalkyl, C$_3$-C$_6$-cycloalkyl, C$_2$-C$_6$-alkenyl, C$_2$-C$_6$-haloalkenyl or C$_2$-C$_6$-alkynyl, C$_1$-C$_6$-alkoxy, C$_2$-C$_6$-alkenyloxy, C$_2$-C$_6$-alkynyloxy, C$_1$-C$_6$-haloalkoxy or C$_1$-C$_6$-alkylthio;

R$^e$, R$^f$ are selected independently from one another from hydrogen, C$_1$-C$_4$-alkyl, C$_1$-C$_4$-haloalkyl, C$_3$-C$_6$-cycloalkyl, C$_3$-C$_6$-alkenyl, C$_3$-C$_6$-haloalkenyl, C$_3$-C$_6$-alkynyl, C(O)R$^c$, C(O)OR$^a$, C(O)NR$^a$R$^b$ or C(S)NR$^a$R$^b$;

m is 0, 1 or 2;

or their agriculturally or veterinarily acceptable salts, enantiomers or diastereomers.

Depending on the substitution pattern, the compounds of formula I can contain one or more chiral centers, in which case they are present as enantiomer or diastereomer mixtures. Subject matter of this invention are not only compositions containing these mixtures but also those containing the pure enantiomers or diastereomers.

The compounds (I) of the present invention can also represent different tautomeric structures. If e.g. R$^3$ is hydrogen, the following two tautomeric structures are represented:

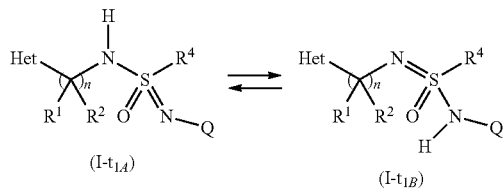

(I-t$_{1A}$)     (I-t$_{1B}$)

If R$^3$ is hydrogen and R$^4$ is NR$^e$R$^f$, and one of R$^e$ or R$^f$ is hydrogen, the following tautomeric structures are further possible:

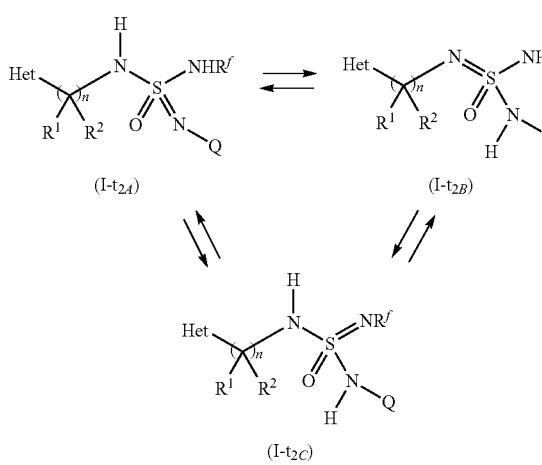

(I-t$_{2A}$)     (I-t$_{2B}$)

(I-t$_{2C}$)

The compounds of formula I of the present invention may also be present in different crystalline modifications which may differ in their biological activity. These are also subject of the present invention.

Herbicidal sulfonimidamide compounds have been described in EP173498. Other general sulfoximine compounds such as arylsulfoximine compounds have been described as herbicide and pesticide in GB 1307271. Pyrazole, pyrrole and imidazole derivatives of sulfoximine compounds and their pesticidal activity can be found in WO 9639389. Isoxazoline derivatives of sulfoximine compounds and their herbicidal activity have been discussed in WO 2006037945. Insecticidal activities of alkyl-substituted sulfoximine compounds can be found in WO 2006060029.

The sulfoximinamid compounds of the formula I, and their agriculturally acceptable salts are highly active against animal pest, i.e. harmful arthropodes and nematodes, especially against difficult to control insects and acaridae.

Accordingly, the present invention relates to sulfoximinamid compounds of the general formula I, to their agriculturally or veterinarily useful salts, their enantiomers or diastereomers.

Moreover, the present invention relates to:
agricultural and veterinary compositions comprising an amount of at least one compound of the formula I or an enantiomer, diasteromer or salt thereof;

the use of a compound of formula I or an enantiomer, diasteromer or salt thereof for combating animal pests;

a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of the formula I or an enantiomer, diasteromer or salt thereof;

a method for protecting crops from attack or infestation by animal pests, which comprises contacting a crop with a pesticidally effective amount of at least one compound of the formula I or an enantiomer, diasteromer or salt thereof;

a method for the protection of seeds from soil insects and of the seedlings' roots and shoots from soil and foliar insects comprising contacting the seeds before sowing and/or after pregermination with at least one compound of the formula I, or the enantiomers, diastereomers or salts thereof;

seeds comprising a compound of the formula I or an enantiomer, diasteromer or salt thereof;

the use of compounds of formula I or the enantiomers, diastereomers or veterinary acceptable salts thereof for combating parasites in and on animals.

a method for treating, controlling, preventing or protecting animals against infestation or infection by parasites which comprises orally, topically or parenterally administering or applying to the animals a parasiticidally effective amount of an compound of formula I or the enantiomers, diastereomers and/or veterinary acceptable salt thereof;

a process for the preparation of a composition for treating, controlling, preventing or protecting animals against infestation or infection by parasites which comprises a parasiticidally effective amount of an compound of formula I or the enantiomers, diastereomers and/or veterinary acceptable salt thereof;

Salts of the compounds of the formula I are preferably agriculturally and/or veterinary acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "3- to 6-membered carbocyclic ring" as used herein refers to cyclopropane, cyclobutane, cyclopentane and cyclohexane rings.

The term "saturated 4-, 5- or 6-membered heterocyclic ring" is illustrated by the following examples:

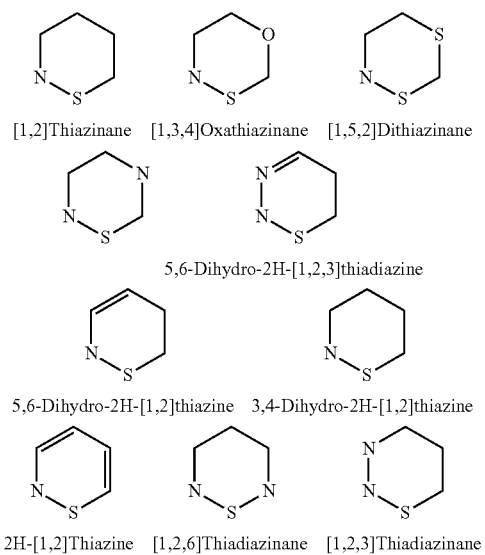

Preferred herein are [1,2]thiazinane compounds.

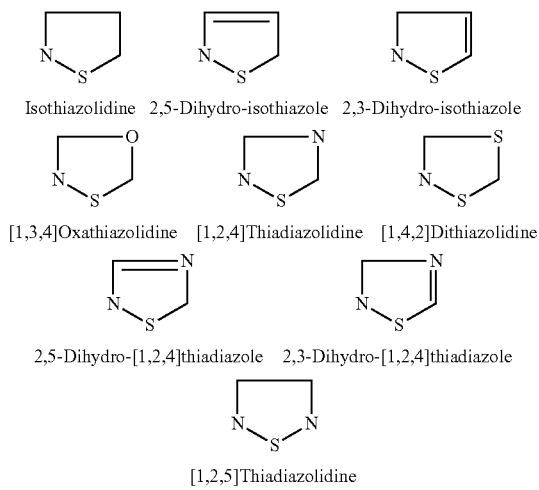

Preferred herein are isothiazolidine compounds.

Preferences

The preferred compounds of the present invention are outlined in the following paragraphs.

Preferred compounds of the present inventions are sulfoximinamide compounds of formula (I), wherein Het is selected from

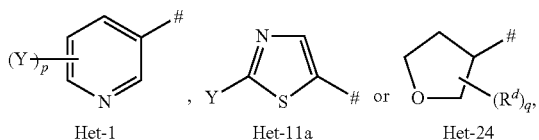

and wherein Y is selected from halogen, $C_1$-$C_4$-haloalkyl or $C_1$-$C_4$-alkyl;

p is 0, 1 or 2;

$R^d$ is selected from halogen, $C_1$-$C_4$-alkyl, $C_1$-$C_4$-haloalkyl, $C_3$-$C_6$-cycloalkyl, $C_2$-$C_6$-alkenyl, $C_2$-$C_6$-haloalkenyl or $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy or $C_1$-$C_6$-alkylthio; and q is 0, 1 or 2.

More preferred compounds of the present invention are sulfoximinamide compounds of formula (I), wherein Het is

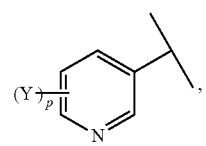

and wherein Y is selected from halogen, $C_1$-$C_4$-haloalkyl or $C_1$-$C_4$-alkyl and p is 0, 1 or 2.

Most preferred compounds of the present invention are sulfoximinamide compounds of formula (I), wherein Het is

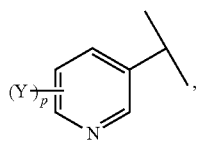

and wherein Y is selected from halogen, $C_1$-$C_4$-haloalkyl or $C_1$-$C_4$-alkyl and p is 1.

Especially preferred are those sulfoximinamide compounds of formula (I), wherein
Het is

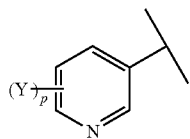

and wherein Y is halogen or $C_1$-$C_4$-haloalkyl and p is 1.

Preferred compounds of the present invention are sulfoximinamide compounds of formula (I), wherein Q is CN.

Preferred compounds of the present invention are sulfoximinamide compounds of formula (I), wherein n is 0 or 1.

More preferred are sulfoximinamide compounds of formula (I), wherein n is 0.

Preferred compounds of the present invention are sulfoximinamide compounds of formula (I), wherein $R^1$ and $R^2$ are independently from one another and independently from n selected from hydrogen, $C_1$-$C_4$-alkyl, $C_1$-$C_4$-haloalkyl or $C_3$-$C_6$-cycloalkyl.

More preferred compounds of the present invention are sulfoximinamide compounds of formula (I), wherein $R^1$ and $R^2$ are independently from one another and independently from n selected from hydrogen, methyl, ethyl or trifluoromethyl.

More preferred are also sulfoximinamide compounds of formula (I), wherein $R^1$ and $R^2$ form cyclopropane together with the carbon atom which they are attached to.

Preferred compounds of the present invention are sulfoximinamide compounds of formula (I), wherein $R^3$ is selected from hydrogen, $C_1$-$C_6$-alkyl, $C_3$-$C_6$-cycloalkyl, $C_1$-$C_6$-haloalkyl or $C_4$-$C_6$-cycloalkylalkyl.

More preferred compounds of the present invention are sulfoximinamide compounds of formula (I), wherein $R^3$ is selected from hydrogen, methyl, ethyl, propyl, isopropyl, cyclopropyl, tert-butyl or cyclopropylmethyl.

Preferred compounds of the present invention are sulfoximinamide compounds of formula (I), wherein $R^4$ is selected from $C_1$-$C_4$-alkyl, $C_3$-$C_4$-cycloalkyl, $C_1$-$C_4$-haloalkyl or cyclopropylmethyl.

More preferred compounds of the present invention are sulfoximinamide compounds of formula (I), wherein $R^4$ is methyl or ethyl.

More preferred are also sulfoximinamide compounds of formula (I), wherein $R^3$ and $R^4$ form together with the nitrogen and sulfur atom they are bond to a saturated or unsaturated 5- or 6-membered heterocyclic ring, whereas the carbon atoms of the heterocyclic ring may optionally carry any combination of 1 or 2 radicals $R^d$, and wherein $R^d$ is selected from halogen, $C_1$-$C_4$-alkyl, $C_1$-$C_4$-haloalkyl, $C_3$-$C_6$-cycloalkyl, $C_2$-$C_6$-alkenyl, $C_2$-$C_6$-haloalkenyl or $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy or $C_1$-$C_6$-alkylthio.

Especially preferred are those sulfoximinamide compounds of formula (I), wherein $R^3$ and $R^4$ form together with the nitrogen and sulfur atom they are bond to a isothiazolidine or [1,2]thiazinane ring.

The following paragraphs show some possible combinations of preferences for illustration. Any combination of preferences are encompassed within the present invention.

Especially preferred compounds of the present invention are sulfoximinamide compounds of formula (I), wherein Het is

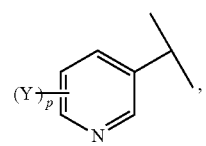

and wherein Y is selected from halogen, $C_1$-$C_4$-haloalkyl or $C_1$-$C_4$-alkyl and p is 0, 1 or 2, wherein Q is CN, n is 0 or 1, $R^1$ and $R^2$ are independently from one another selected from hydrogen, methyl, ethyl or trifluoromethyl, or $R^1$ and $R^2$ form cyclopropane together with the carbon atom which they are attached to, $R^3$ is selected from hydrogen, methyl, ethyl, propyl, isopropyl, cyclopropyl, tert-butyl or cyclopropylmethyl and $R^4$ is methyl or ethyl, or $R^3$ and $R^4$ form together with the nitrogen and sulfur atom they are bond to a saturated or unsaturated 4-, 5- or 6-membered heterocyclic ring, optionally containing an additional heteroatom selected from N, O, S, whereas the carbon atoms of the heterocyclic ring may optionally carry any combination of 1 or 2 radicals $R^d$ and whereas the additional N atom optionally may carry $R^e$, and wherein $R^d$ is selected from halogen, $C_1$-$C_4$-alkyl, $C_1$-$C_4$haloalkyl, $C_3$-$C_6$-cycloalkyl, $C_2$-$C_6$-alkenyl, $C_2$-$C_6$-haloalkenyl or $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy or $C_1$-$C_6$-alkylthio and $R^e$ is selected from hydrogen, $C_1$-$C_4$-alkyl, $C_1$-$C_4$-haloalkyl, $C_3$-$C_6$-cycloalkyl, $C_3$-$C_6$-alkenyl, $C_3$-$C_6$-haloalkenyl, $C_3$-$C_6$-alkynyl, C(O)$R^c$, C(O)O$R^a$, C(O)N$R^a R^b$ or C(S)N$R^a R^b$.

Especially preferred compounds of the present invention are sulfoximinamide compounds of formula (I), wherein Het is

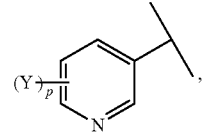

and wherein Y is selected from fluoro, chloro, bromo, jodo or a $C_1$-$C_4$-haloalkyl and p is 1, wherein Q is CN, n is 0, $R^3$ is selected from hydrogen, methyl, ethyl, propyl, isopropyl, cyclopropyl, tert-butyl or cyclopropylmethyl and $R^4$ is methyl or ethyl, or $R^3$ and $R^4$ form together with the nitrogen and sulfur atom they are bond to a saturated or unsaturated 4-, 5- or 6-membered heterocyclic ring, optionally containing an additional heteroatom selected from N, O, S, whereas the carbon atoms of the heterocyclic ring may optionally carry any combination of 1 or 2 radicals $R^d$ and whereas the additional N atom optionally may carry $R^e$, and wherein $R^d$ is selected from halogen, $C_1$-$C_4$-alkyl, $C_1$-$C_4$-haloalkyl, $C_3$-$C_6$-cycloalkyl, $C_2$-$C_6$-alkenyl, $C_2$-$C_6$-haloalkenyl or $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy or $C_1$-$C_6$-alkylthio and $R^e$ is selected from hydrogen, $C_1$-$C_4$-alkyl, $C_1$-$C_4$-haloalkyl, $C_3$-$C_6$-cycloalkyl, $C_3$-$C_6$-alkenyl, $C_3$-$C_6$-haloalkenyl, $C_3$-$C_6$-alkynyl, $C(O)R^c$, $C(O)OR^a$, $C(O)NR^aR^b$ or $C(S)NR^aR^b$.

Especially preferred compounds of the present invention are sulfoximine compounds of formula (I), wherein Het is

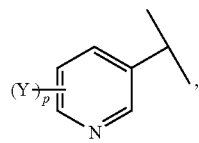

and wherein Y is selected from halogen or $C_1$-$C_4$-haloalkyl and p is 1, Q is CN, n is 0 and $R^3$ and $R^4$ form together with the nitrogen and sulfur atom they are bond to an unsubstituted isothiazolidine or an unsubstituted [1,2]thiazinane ring.

Examples of Preferred Compounds

Examples of such especially preferred compounds are compounds of formula (I-A), wherein $R^1$, $R^2$, $R^3$, $R^4$ and Het have the meanings given in any of lines C.1 to C.308 of table C.I.

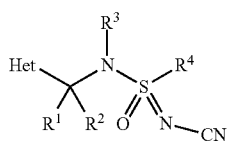
(I-A)

Examples of such especially preferred compounds are also compounds of formula (I-B), wherein $R^1$, $R^2$, $R^3$, $R^4$ and Het have the meanings given in any of lines C.1 to C.308 of table C.I.

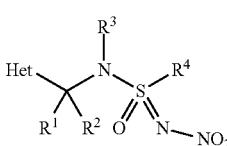
(I-B)

TABLE C.I

| No | Het | $R^1$ | $R^2$ | $R^3$ | $R^4$ |
|----|-----|-------|-------|-------|-------|
| C.1. | 6-Cl-pyridin-3-yl (#) | H | H | H | CH$_3$ |
| C.2. | 6-F$_3$C-pyridin-3-yl (#) | H | H | H | CH$_3$ |
| C.3. | 6-ClF$_2$C-pyridin-3-yl (#) | H | H | H | CH$_3$ |
| C.4. | 6-Cl$_3$C-pyridin-3-yl (#) | H | H | H | CH$_3$ |
| C.5. | 6-HF$_2$C-pyridin-3-yl (#) | H | H | H | CH$_3$ |
| C.6. | 6-(CF$_2$CH$_3$)-pyridin-3-yl (#) | H | H | H | CH$_3$ |
| C.7. | 5,6-diCl-pyridin-3-yl (#) | H | H | H | CH$_3$ |
| C.8. | 5-F-6-Cl-pyridin-3-yl (#) | H | H | H | CH$_3$ |
| C.9. | 2-Cl-thiazol-5-yl (#) | H | H | H | CH$_3$ |
| C.10. | 2-F$_3$C-thiazol-5-yl (#) | H | H | H | CH$_3$ |
| C.11. | tetrahydrofuran-3-yl (#) | H | H | H | CH$_3$ |
| C.12. | 6-Cl-pyridin-3-yl (#) | H | H | H | C$_2$H$_5$ |
| C.13. | 6-F$_3$C-pyridin-3-yl (#) | H | H | H | C$_2$H$_5$ |
| C.14. | 6-ClF$_2$C-pyridin-3-yl (#) | H | H | H | C$_2$H$_5$ |

TABLE C.I-continued
| No | Het | R¹ | R² | R³ | R⁴ |
|---|---|---|---|---|---|
| C.15. | 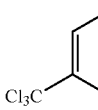 | H | H | H | $C_2H_5$ |
| C.16. | 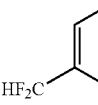 | H | H | H | $C_2H_5$ |
| C.17. | 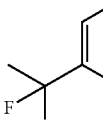 | H | H | H | $C_2H_5$ |
| C.18. | 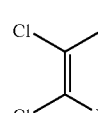 | H | H | H | $C_2H_5$ |
| C.19. | 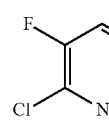 | H | H | H | $C_2H_5$ |
| C.20. | 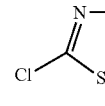 | H | H | H | $C_2H_5$ |
| C.21. | 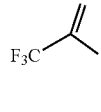 | H | H | H | $C_2H_5$ |
| C.22. |  | H | H | H | $C_2H_5$ |
| C.23. | 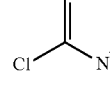 | H | H | $CH_3$ | $CH_3$ |
| C.24. | 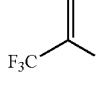 | H | H | $CH_3$ | $CH_3$ |
| C.25. | 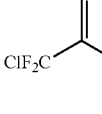 | H | H | $CH_3$ | $CH_3$ |
| C.26. | 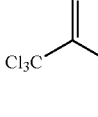 | H | H | $CH_3$ | $CH_3$ |
| C.27. | 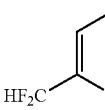 | H | H | $CH_3$ | $CH_3$ |
| C.28. | 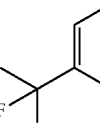 | H | H | $CH_3$ | $CH_3$ |
| C.29. | 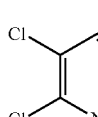 | H | H | $CH_3$ | $CH_3$ |
| C.30. | 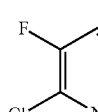 | H | H | $CH_3$ | $CH_3$ |
| C.31. | 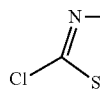 | H | H | $CH_3$ | $CH_3$ |
| C.32. | 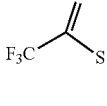 | H | H | $CH_3$ | $CH_3$ |
| C.33. | 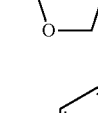 | H | H | $CH_3$ | $CH_3$ |
| C.34. |  | H | H | $CH_3$ | $C_2H_5$ |
| C.35. | 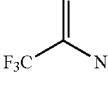 | H | H | $CH_3$ | $C_2H_5$ |
| C.36. | 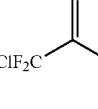 | H | H | $CH_3$ | $C_2H_5$ |
| C.37. | 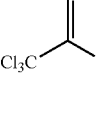 | H | H | $CH_3$ | $C_2H_5$ |
| C.38. | 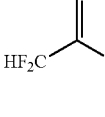 | H | H | $CH_3$ | $C_2H_5$ |

TABLE C.I-continued
| No | Het | R¹ | R² | R³ | R⁴ |
|---|---|---|---|---|---|
| C.39. | 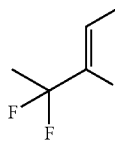 | H | H | CH₃ | C₂H₅ |
| C.40. | 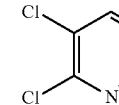 | H | H | CH₃ | C₂H₅ |
| C.41. | 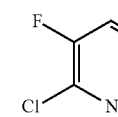 | H | H | CH₃ | C₂H₅ |
| C.42. | 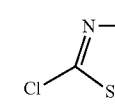 | H | H | CH₃ | C₂H₅ |
| C.43. | 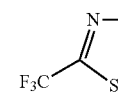 | H | H | CH₃ | C₂H₅ |
| C.44. | 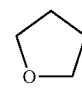 | H | H | CH₃ | C₂H₅ |
| C.45. | 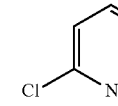 | H | H | C₂H₅ | CH₃ |
| C.46. | 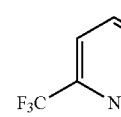 | H | H | C₂H₅ | CH₃ |
| C.47. | 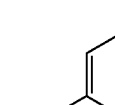 | H | H | C₂H₅ | CH₃ |
| C.48. | 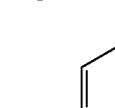 | H | H | C₂H₅ | CH₃ |
| C.49. | 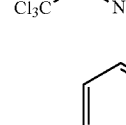 | H | H | C₂H₅ | CH₃ |
| C.50. | 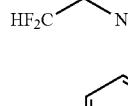 | H | H | C₂H₅ | CH₃ |
| C.51. | 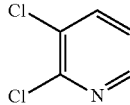 | H | H | C₂H₅ | CH₃ |
| C.52. | 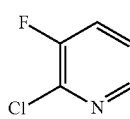 | H | H | C₂H₅ | CH₃ |
| C.53. | 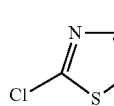 | H | H | C₂H₅ | CH₃ |
| C.54. | 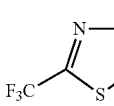 | H | H | C₂H₅ | CH₃ |
| C.55. | 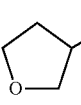 | H | H | C₂H₅ | CH₃ |
| C.56. | 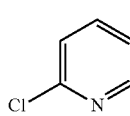 | H | H | C₂H₅ | C₂H₅ |
| C.57. | 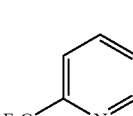 | H | H | C₂H₅ | C₂H₅ |
| C.58. | 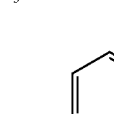 | H | H | C₂H₅ | C₂H₅ |
| C.59. | 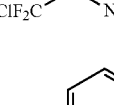 | H | H | C₂H₅ | C₂H₅ |
| C.60. | 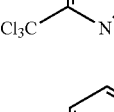 | H | H | C₂H₅ | C₂H₅ |
| C.61. | 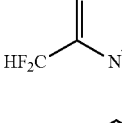 | H | H | C₂H₅ | C₂H₅ |
| C.62. | 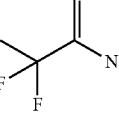 | H | H | C₂H₅ | C₂H₅ |

TABLE C.I-continued

| No | Het | R¹ | R² | R³ | R⁴ |
|---|---|---|---|---|---|
| C.63. | 3-F, 2-Cl pyridin-5-yl | H | H | C₂H₅ | C₂H₅ |
| C.64. | 2-Cl thiazol-5-yl | H | H | C₂H₅ | C₂H₅ |
| C.65. | 2-CF₃ thiazol-5-yl | H | H | C₂H₅ | C₂H₅ |
| C.66. | tetrahydrofuran-3-yl | H | H | C₂H₅ | C₂H₅ |
| C.67. | 2-Cl pyridin-5-yl | H | H | CH₂—CH₂—CH₂ | |
| C.68. | 2-CF₃ pyridin-5-yl | H | H | CH₂—CH₂—CH₂ | |
| C.69. | 2-ClF₂C pyridin-5-yl | H | H | CH₂—CH₂—CH₂ | |
| C.70. | 2-Cl₃C pyridin-5-yl | H | H | CH₂—CH₂—CH₂ | |
| C.71. | 2-HF₂C pyridin-5-yl | H | H | CH₂—CH₂—CH₂ | |
| C.72. | 2-(CHF₂CH) pyridin-5-yl | H | H | CH₂—CH₂—CH₂ | |
| C.73. | 2,3-diCl pyridin-5-yl | H | H | CH₂—CH₂—CH₂ | |
| C.74. | 3-F, 2-Cl pyridin-5-yl | H | H | CH₂—CH₂—CH₂ | |
| C.75. | 2-Cl thiazol-5-yl | H | H | CH₂—CH₂—CH₂ | |
| C.76. | 2-CF₃ thiazol-5-yl | H | H | CH₂—CH₂—CH₂ | |
| C.77. | tetrahydrofuran-3-yl | H | H | CH₂—CH₂—CH₂ | |
| C.78. | 2-Cl pyridin-5-yl | H | CH₃ | H | CH₃ |
| C.79. | 2-CF₃ pyridin-5-yl | H | CH₃ | H | CH₃ |
| C.80. | 2-ClF₂C pyridin-5-yl | H | CH₃ | H | CH₃ |
| C.81. | 2-Cl₃C pyridin-5-yl | H | CH₃ | H | CH₃ |
| C.82. | 2-HF₂C pyridin-5-yl | H | CH₃ | H | CH₃ |
| C.83. | 2-(CHF₂CH) pyridin-5-yl | H | CH₃ | H | CH₃ |
| C.84. | 2,3-diCl pyridin-5-yl | H | CH₃ | H | CH₃ |
| C.85. | 3-F, 2-Cl pyridin-5-yl | H | CH₃ | H | CH₃ |
| C.86. | 2-Cl thiazol-5-yl | H | CH₃ | H | CH₃ |
| C.87. | 2-CF₃ thiazol-5-yl | H | CH₃ | H | CH₃ |

TABLE C.I-continued

| No | Het | R¹ | R² | R³ | R⁴ |
|---|---|---|---|---|---|
| C.88. | tetrahydrofuran-3-yl | H | CH₃ | H | CH₃ |
| C.89. | 6-chloropyridin-3-yl | H | CH₃ | H | C₂H₅ |
| C.90. | 6-(trifluoromethyl)pyridin-3-yl | H | CH₃ | H | C₂H₅ |
| C.91. | 6-(chlorodifluoromethyl)pyridin-3-yl | H | CH₃ | H | C₂H₅ |
| C.92. | 6-(trichloromethyl)pyridin-3-yl | H | CH₃ | H | C₂H₅ |
| C.93. | 6-(difluoromethyl)pyridin-3-yl | H | CH₃ | H | C₂H₅ |
| C.94. | 6-(1,1-difluoroethyl)pyridin-3-yl | H | CH₃ | H | C₂H₅ |
| C.95. | 5,6-dichloropyridin-3-yl | H | CH₃ | H | C₂H₅ |
| C.96. | 5-fluoro-6-chloropyridin-3-yl | H | CH₃ | H | C₂H₅ |
| C.97. | 2-chlorothiazol-5-yl | H | CH₃ | H | C₂H₅ |
| C.98. | 2-(trifluoromethyl)thiazol-5-yl | H | CH₃ | H | C₂H₅ |
| C.99. | tetrahydrofuran-3-yl | H | CH₃ | H | C₂H₅ |
| C.100. | 6-chloropyridin-3-yl | H | CH₃ | CH₃ | CH₃ |
| C.101. | 6-(trifluoromethyl)pyridin-3-yl | H | CH₃ | CH₃ | CH₃ |
| C.102. | 6-(chlorodifluoromethyl)pyridin-3-yl | H | CH₃ | CH₃ | CH₃ |
| C.103. | 6-(trichloromethyl)pyridin-3-yl | H | CH₃ | CH₃ | CH₃ |
| C.104. | 6-(difluoromethyl)pyridin-3-yl | H | CH₃ | CH₃ | CH₃ |
| C.105. | 6-(1,1-difluoroethyl)pyridin-3-yl | H | CH₃ | CH₃ | CH₃ |
| C.106. | 5,6-dichloropyridin-3-yl | H | CH₃ | CH₃ | CH₃ |
| C.107. | 5-fluoro-6-chloropyridin-3-yl | H | CH₃ | CH₃ | CH₃ |
| C.108. | 2-chlorothiazol-5-yl | H | CH₃ | CH₃ | CH₃ |
| C.109. | 2-(trifluoromethyl)thiazol-5-yl | H | CH₃ | CH₃ | CH₃ |
| C.110. | tetrahydrofuran-3-yl | H | CH₃ | CH₃ | CH₃ |
| C.111. | 6-chloropyridin-3-yl | H | CH₃ | CH₃ | C₂H₅ |

TABLE C.I-continued

| No | Het | R¹ | R² | R³ | R⁴ |
|---|---|---|---|---|---|
| C.112. | 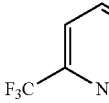 | H | CH₃ | CH₃ | C₂H₅ |
| C.113. | 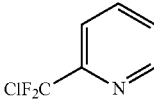 | H | CH₃ | CH₃ | C₂H₅ |
| C.114. | 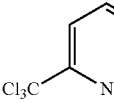 | H | CH₃ | CH₃ | C₂H₅ |
| C.115. | 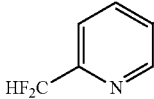 | H | CH₃ | CH₃ | C₂H₅ |
| C.116. | 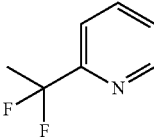 | H | CH₃ | CH₃ | C₂H₅ |
| C.117. | 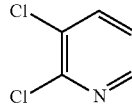 | H | CH₃ | CH₃ | C₂H₅ |
| C.118. | 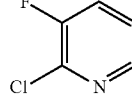 | H | CH₃ | CH₃ | C₂H₅ |
| C.119. | 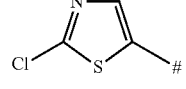 | H | CH₃ | CH₃ | C₂H₅ |
| C.120. | 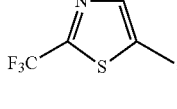 | H | CH₃ | CH₃ | C₂H₅ |
| C.121. | 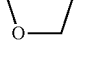 | H | CH₃ | CH₃ | C₂H₅ |
| C.122. | 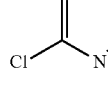 | H | CH₃ | C₂H₅ | CH₃ |
| C.123. | 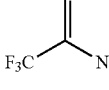 | H | CH₃ | C₂H₅ | CH₃ |
| C.124. | 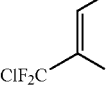 | H | CH₃ | C₂H₅ | CH₃ |
| C.125. | 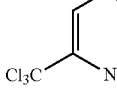 | H | CH₃ | C₂H₅ | CH₃ |
| C.126. | 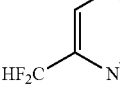 | H | CH₃ | C₂H₅ | CH₃ |
| C.127. | 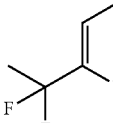 | H | CH₃ | C₂H₅ | CH₃ |
| C.128. | 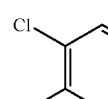 | H | CH₃ | C₂H₅ | CH₃ |
| C.129. | 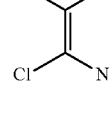 | H | CH₃ | C₂H₅ | CH₃ |
| C.130. | 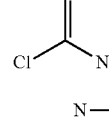 | H | CH₃ | C₂H₅ | CH₃ |
| C.131. | 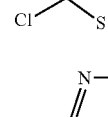 | H | CH₃ | C₂H₅ | CH₃ |
| C.132. | 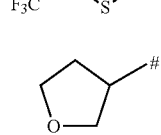 | H | CH₃ | C₂H₅ | CH₃ |
| C.133. |  | H | CH₃ | C₂H₅ | C₂H₅ |
| C.134. | 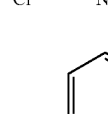 | H | CH₃ | C₂H₅ | C₂H₅ |
| C.135. | 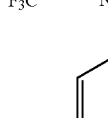 | H | CH₃ | C₂H₅ | C₂H₅ |

TABLE C.I-continued

| No | Het | R¹ | R² | R³ | R⁴ |
|---|---|---|---|---|---|
| C.136. | 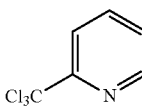 | H | CH₃ | C₂H₅ | C₂H₅ |
| C.137. | 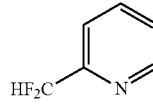 | H | CH₃ | C₂H₅ | C₂H₅ |
| C.138. |  | H | CH₃ | C₂H₅ | C₂H₅ |
| C.139. | 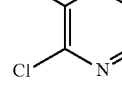 | H | CH₃ | C₂H₅ | C₂H₅ |
| C.140. | 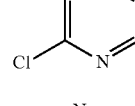 | H | CH₃ | C₂H₅ | C₂H₅ |
| C.141. | 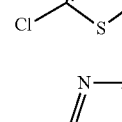 | H | CH₃ | C₂H₅ | C₂H₅ |
| C.142. | 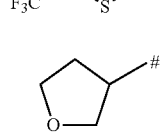 | H | CH₃ | C₂H₅ | C₂H₅ |
| C.143. |  | H | CH₃ | C₂H₅ | C₂H₅ |
| C.144. | 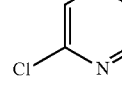 | H | CH₃ | CH₂—CH₂—CH₂ | |
| C.145. | 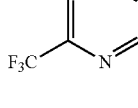 | H | CH₃ | CH₂—CH₂—CH₂ | |
| C.146. | 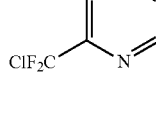 | H | CH₃ | CH₂—CH₂—CH₂ | |
| C.147. | 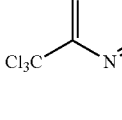 | H | CH₃ | CH₂—CH₂—CH₂ | |
| C.148. | 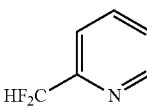 | H | CH₃ | CH₂—CH₂—CH₂ | |
| C.149. | 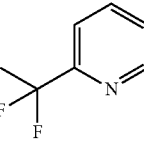 | H | CH₃ | CH₂—CH₂—CH₂ | |
| C.150. | 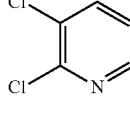 | H | CH₃ | CH₂—CH₂—CH₂ | |
| C.151. | 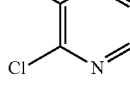 | H | CH₃ | CH₂—CH₂—CH₂ | |
| C.152. | 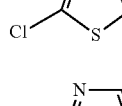 | H | CH₃ | CH₂—CH₂—CH₂ | |
| C.153. | 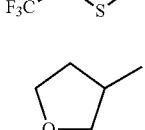 | H | CH₃ | CH₂—CH₂—CH₂ | |
| C.154. | 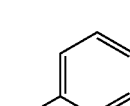 | H | CH₃ | CH₂—CH₂—CH₂ | |
| C.155. |  | CH₂—CH₂ | H | CH₃ | |
| C.156. | 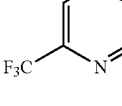 | CH₂—CH₂ | H | CH₃ | |
| C.157. | 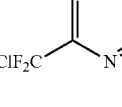 | CH₂—CH₂ | H | CH₃ | |
| C.158. | 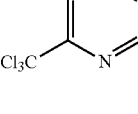 | CH₂—CH₂ | H | CH₃ | |
| C.159. | 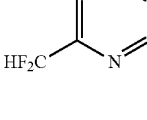 | CH₂—CH₂ | H | CH₃ | |

TABLE C.I-continued

| No | Het | R¹ | R² | R³ | R⁴ |
|---|---|---|---|---|---|
| C.160. | 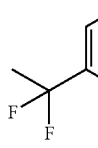 | CH$_2$—CH$_2$ | H | CH$_3$ |
| C.161. | 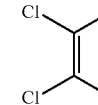 | CH$_2$—CH$_2$ | H | CH$_3$ |
| C.162. | 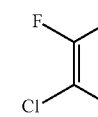 | CH$_2$—CH$_2$ | H | CH$_3$ |
| C.163. | 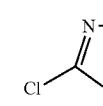 | CH$_2$—CH$_2$ | H | CH$_3$ |
| C.164. | 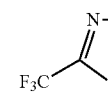 | CH$_2$—CH$_2$ | H | CH$_3$ |
| C.165. | 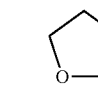 | CH$_2$—CH$_2$ | H | CH$_3$ |
| C.166. | 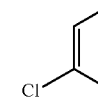 | CH$_2$—CH$_2$ | H | C$_2$H$_5$ |
| C.167. | 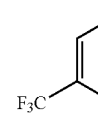 | CH$_2$—CH$_2$ | H | C$_2$H$_5$ |
| C.168. | 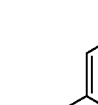 | CH$_2$—CH$_2$ | H | C$_2$H$_5$ |
| C.169. | 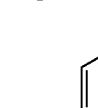 | CH$_2$—CH$_2$ | H | C$_2$H$_5$ |
| C.170. | 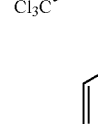 | CH$_2$—CH$_2$ | H | C$_2$H$_5$ |
| C.171. | 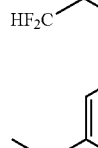 | CH$_2$—CH$_2$ | H | C$_2$H$_5$ |
| C.172. | 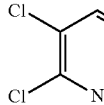 | CH$_2$—CH$_2$ | H | C$_2$H$_5$ |
| C.173. | 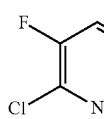 | CH$_2$—CH$_2$ | H | C$_2$H$_5$ |
| C.174. | 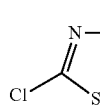 | CH$_2$—CH$_2$ | H | C$_2$H$_5$ |
| C.175. | 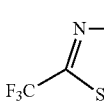 | CH$_2$—CH$_2$ | H | C$_2$H$_5$ |
| C.176. | 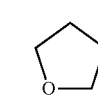 | CH$_2$—CH$_2$ | H | C$_2$H$_5$ |
| C.177. | 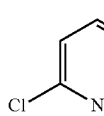 | CH$_2$—CH$_2$ | CH$_3$ | CH$_3$ |
| C.178. | 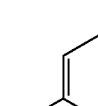 | CH$_2$—CH$_2$ | CH$_3$ | CH$_3$ |
| C.179. | 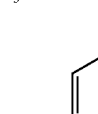 | CH$_2$—CH$_2$ | CH$_3$ | CH$_3$ |
| C.180. | 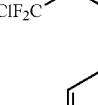 | CH$_2$—CH$_2$ | CH$_3$ | CH$_3$ |
| C.181. | 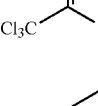 | CH$_2$—CH$_2$ | CH$_3$ | CH$_3$ |
| C.182. | 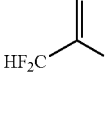 | CH$_2$—CH$_2$ | CH$_3$ | CH$_3$ |
| C.183. | 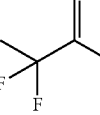 | CH$_2$—CH$_2$ | CH$_3$ | CH$_3$ |

| No | Het | R¹ | R² | R³ | R⁴ |
|---|---|---|---|---|---|
| C.184. | 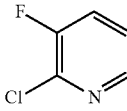 | | CH₂—CH₂ | CH₃ | CH₃ |
| C.185. | 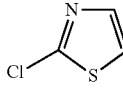 | | CH₂—CH₂ | CH₃ | CH₃ |
| C.186. | 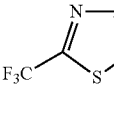 | | CH₂—CH₂ | CH₃ | CH₃ |
| C.187. |  | | CH₂—CH₂ | CH₃ | CH₃ |
| C.188. | 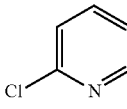 | | CH₂—CH₂ | CH₃ | C₂H₅ |
| C.189. | 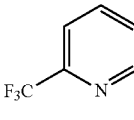 | | CH₂—CH₂ | CH₃ | C₂H₅ |
| C.190. | 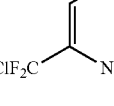 | | CH₂—CH₂ | CH₃ | C₂H₅ |
| C.191. | 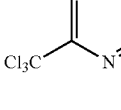 | | CH₂—CH₂ | CH₃ | C₂H₅ |
| C.192. | 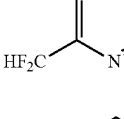 | | CH₂—CH₂ | CH₃ | C₂H₅ |
| C.193. | 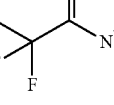 | | CH₂—CH₂ | CH₃ | C₂H₅ |
| C.194. | 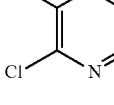 | | CH₂—CH₂ | CH₃ | C₂H₅ |
| C.195. | 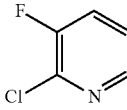 | | CH₂—CH₂ | CH₃ | C₂H₅ |
| C.196. | 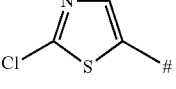 | | CH₂—CH₂ | CH₃ | C₂H₅ |
| C.197. | 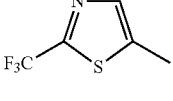 | | CH₂—CH₂ | CH₃ | C₂H₅ |
| C.198. | 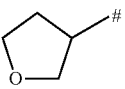 | | CH₂—CH₂ | CH₃ | C₂H₅ |
| C.199. | 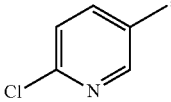 | | CH₂—CH₂ | C₂H₅ | CH₃ |
| C.200. | 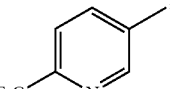 | | CH₂—CH₂ | C₂H₅ | CH₃ |
| C.201. | 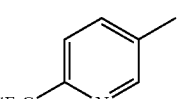 | | CH₂—CH₂ | C₂H₅ | CH₃ |
| C.202. | 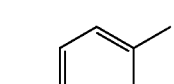 | | CH₂—CH₂ | C₂H₅ | CH₃ |
| C.203. | 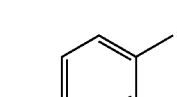 | | CH₂—CH₂ | C₂H₅ | CH₃ |
| C.204. | 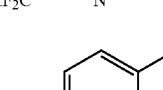 | | CH₂—CH₂ | C₂H₅ | CH₃ |
| C.205. | 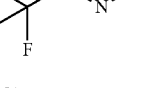 | | CH₂—CH₂ | C₂H₅ | CH₃ |
| C.206. | 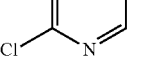 | | CH₂—CH₂ | C₂H₅ | CH₃ |
| C.207. | 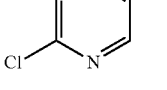 | | CH₂—CH₂ | C₂H₅ | CH₃ |
| C.208. | | | CH₂—CH₂ | C₂H₅ | CH₃ |

TABLE C.I-continued

| No | Het | R¹ | R² | R³ | R⁴ |
|---|---|---|---|---|---|
| C.209. | tetrahydrofuran-3-yl (#) | | CH₂—CH₂ | C₂H₅ | CH₃ |
| C.210. | 6-chloropyridin-3-yl (#) | | CH₂—CH₂ | C₂H₅ | C₂H₅ |
| C.211. | 6-(trifluoromethyl)pyridin-3-yl (#) | | CH₂—CH₂ | C₂H₅ | C₂H₅ |
| C.212. | 6-(chlorodifluoromethyl)pyridin-3-yl (#) | | CH₂—CH₂ | C₂H₅ | C₂H₅ |
| C.213. | 6-(trichloromethyl)pyridin-3-yl (#) | | CH₂—CH₂ | C₂H₅ | C₂H₅ |
| C.214. | 6-(difluoromethyl)pyridin-3-yl (#) | | CH₂—CH₂ | C₂H₅ | C₂H₅ |
| C.215. | 6-(1,1-difluoroethyl)pyridin-3-yl (#) | | CH₂—CH₂ | C₂H₅ | C₂H₅ |
| C.216. | 5,6-dichloropyridin-3-yl (#) | | CH₂—CH₂ | C₂H₅ | C₂H₅ |
| C.217. | 5-fluoro-6-chloropyridin-3-yl (#) | | CH₂—CH₂ | C₂H₅ | C₂H₅ |
| C.218. | 2-chlorothiazol-5-yl (#) | | CH₂—CH₂ | C₂H₅ | C₂H₅ |
| C.219. | 2-(trifluoromethyl)thiazol-5-yl (#) | | CH₂—CH₂ | C₂H₅ | C₂H₅ |
| C.220. | tetrahydrofuran-3-yl (#) | | CH₂—CH₂ | C₂H₅ | C₂H₅ |
| C.221. | 6-chloropyridin-3-yl (#) | | CH₂—CH₂ | CH₂—CH₂—CH₂ | |
| C.222. | 6-(trifluoromethyl)pyridin-3-yl (#) | | CH₂—CH₂ | CH₂—CH₂—CH₂ | |
| C.223. | 6-(chlorodifluoromethyl)pyridin-3-yl (#) | | CH₂—CH₂ | CH₂—CH₂—CH₂ | |
| C.224. | 6-(trichloromethyl)pyridin-3-yl (#) | | CH₂—CH₂ | CH₂—CH₂—CH₂ | |
| C.225. | 6-(difluoromethyl)pyridin-3-yl (#) | | CH₂—CH₂ | CH₂—CH₂—CH₂ | |
| C.226. | 6-(1,1-difluoroethyl)pyridin-3-yl (#) | | CH₂—CH₂ | CH₂—CH₂—CH₂ | |
| C.227. | 5,6-dichloropyridin-3-yl (#) | | CH₂—CH₂ | CH₂—CH₂—CH₂ | |
| C.228. | 5-fluoro-6-chloropyridin-3-yl (#) | | CH₂—CH₂ | CH₂—CH₂—CH₂ | |
| C.229. | 2-chlorothiazol-5-yl (#) | | CH₂—CH₂ | CH₂—CH₂—CH₂ | |
| C.230. | 2-(trifluoromethyl)thiazol-5-yl (#) | | CH₂—CH₂ | CH₂—CH₂—CH₂ | |
| C.231. | tetrahydrofuran-3-yl (#) | | CH₂—CH₂ | CH₂—CH₂—CH₂ | |
| C.232. | 6-chloropyridin-3-yl (#) | CH₃ | CH₃ | H | CH₃ |

TABLE C.I-continued

| No | Het | R¹ | R² | R³ | R⁴ |
|---|---|---|---|---|---|
| C.233. | 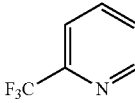 | CH₃ | CH₃ | H | CH₃ |
| C.234. | 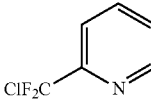 | CH₃ | CH₃ | H | CH₃ |
| C.235. | 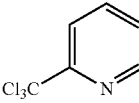 | CH₃ | CH₃ | H | CH₃ |
| C.236. | 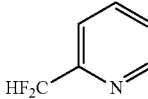 | CH₃ | CH₃ | H | CH₃ |
| C.237. |  | CH₃ | CH₃ | H | CH₃ |
| C.238. | 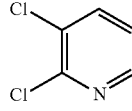 | CH₃ | CH₃ | H | CH₃ |
| C.239. | 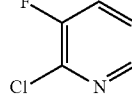 | CH₃ | CH₃ | H | CH₃ |
| C.240. | 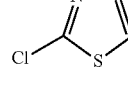 | CH₃ | CH₃ | H | CH₃ |
| C.241. | 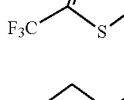 | CH₃ | CH₃ | H | CH₃ |
| C.242. |  | CH₃ | CH₃ | H | CH₃ |
| C.243. | 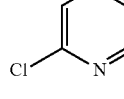 | CH₃ | CH₃ | H | C₂H₅ |
| C.244. | 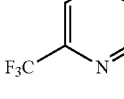 | CH₃ | CH₃ | H | C₂H₅ |
| C.245. | 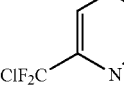 | CH₃ | CH₃ | H | C₂H₅ |
| C.246. | 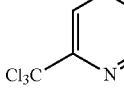 | CH₃ | CH₃ | H | C₂H₅ |
| C.247. | 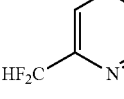 | CH₃ | CH₃ | H | C₂H₅ |
| C.248. | 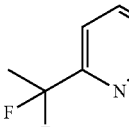 | CH₃ | CH₃ | H | C₂H₅ |
| C.249. | 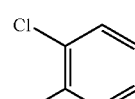 | CH₃ | CH₃ | H | C₂H₅ |
| C.250. | 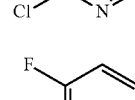 | CH₃ | CH₃ | H | C₂H₅ |
| C.251. | 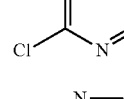 | CH₃ | CH₃ | H | C₂H₅ |
| C.252. | 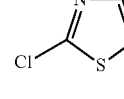 | CH₃ | CH₃ | H | C₂H₅ |
| C.253. | 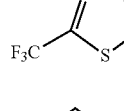 | CH₃ | CH₃ | H | C₂H₅ |
| C.254. |  | CH₃ | CH₃ | CH₃ | CH₃ |
| C.255. | 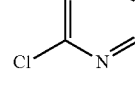 | CH₃ | CH₃ | CH₃ | CH₃ |
| C.256. | 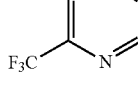 | CH₃ | CH₃ | CH₃ | CH₃ |

TABLE C.I-continued

| No | Het | R¹ | R² | R³ | R⁴ |
|---|---|---|---|---|---|
| C.257. | 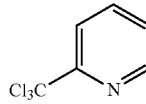 | CH₃ | CH₃ | CH₃ | CH₃ |
| C.258. | 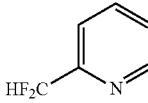 | CH₃ | CH₃ | CH₃ | CH₃ |
| C.259. |  | CH₃ | CH₃ | CH₃ | CH₃ |
| C.260. | 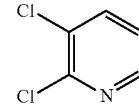 | CH₃ | CH₃ | CH₃ | CH₃ |
| C.261. | 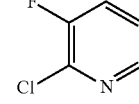 | CH₃ | CH₃ | CH₃ | CH₃ |
| C.262. | 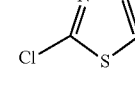 | CH₃ | CH₃ | CH₃ | CH₃ |
| C.263. | 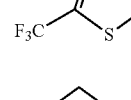 | CH₃ | CH₃ | CH₃ | CH₃ |
| C.264. | 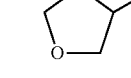 | CH₃ | CH₃ | CH₃ | CH₃ |
| C.265. | 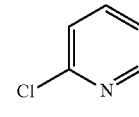 | CH₃ | CH₃ | CH₃ | C₂H₅ |
| C.266. | 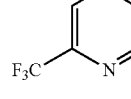 | CH₃ | CH₃ | CH₃ | C₂H₅ |
| C.267. | 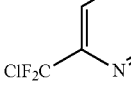 | CH₃ | CH₃ | CH₃ | C₂H₅ |
| C.268. | 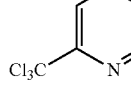 | CH₃ | CH₃ | CH₃ | C₂H₅ |
| C.269. | 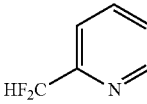 | CH₃ | CH₃ | CH₃ | C₂H₅ |
| C.270. | 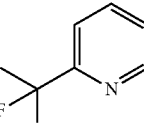 | CH₃ | CH₃ | CH₃ | C₂H₅ |
| C.271. |  | CH₃ | CH₃ | CH₃ | C₂H₅ |
| C.272. |  | CH₃ | CH₃ | CH₃ | C₂H₅ |
| C.273. |  | CH₃ | CH₃ | CH₃ | C₂H₅ |
| C.274. |  | CH₃ | CH₃ | CH₃ | C₂H₅ |
| C.275. |  | CH₃ | CH₃ | CH₃ | C₂H₅ |
| C.276. |  | CH₃ | CH₃ | C₂H₅ | CH₃ |
| C.277. |  | CH₃ | CH₃ | C₂H₅ | CH₃ |
| C.278. |  | CH₃ | CH₃ | C₂H₅ | CH₃ |
| C.279. |  | CH₃ | CH₃ | C₂H₅ | CH₃ |
| C.280. |  | CH₃ | CH₃ | C₂H₅ | CH₃ |

TABLE C.I-continued

| No | Het | R¹ | R² | R³ | R⁴ |
|---|---|---|---|---|---|
| C.281. | 2-(1,1-difluoroethyl)pyridin-5-yl | CH₃ | CH₃ | C₂H₅ | CH₃ |
| C.282. | 5,6-dichloropyridin-3-yl | CH₃ | CH₃ | C₂H₅ | CH₃ |
| C.283. | 5-fluoro-6-chloropyridin-3-yl | CH₃ | CH₃ | C₂H₅ | CH₃ |
| C.284. | 2-chlorothiazol-5-yl | CH₃ | CH₃ | C₂H₅ | CH₃ |
| C.285. | 2-(trifluoromethyl)thiazol-5-yl | CH₃ | CH₃ | C₂H₅ | CH₃ |
| C.286. | tetrahydrofuran-3-yl | CH₃ | CH₃ | C₂H₅ | CH₃ |
| C.287. | 6-chloropyridin-3-yl | CH₃ | CH₃ | C₂H₅ | C₂H₅ |
| C.288. | 6-(trifluoromethyl)pyridin-3-yl | CH₃ | CH₃ | C₂H₅ | C₂H₅ |
| C.289. | 6-(chlorodifluoromethyl)pyridin-3-yl | CH₃ | CH₃ | C₂H₅ | C₂H₅ |
| C.290. | 6-(trichloromethyl)pyridin-3-yl | CH₃ | CH₃ | C₂H₅ | C₂H₅ |
| C.291. | 6-(difluoromethyl)pyridin-3-yl | CH₃ | CH₃ | C₂H₅ | C₂H₅ |
| C.292. | 6-(1,1-difluoroethyl)pyridin-3-yl | CH₃ | CH₃ | C₂H₅ | C₂H₅ |
| C.293. | 5,6-dichloropyridin-3-yl | CH₃ | CH₃ | C₂H₅ | C₂H₅ |
| C.294. | 5-fluoro-6-chloropyridin-3-yl | CH₃ | CH₃ | C₂H₅ | C₂H₅ |
| C.295. | 2-chlorothiazol-5-yl | CH₃ | CH₃ | C₂H₅ | C₂H₅ |
| C.296. | 2-(trifluoromethyl)thiazol-5-yl | CH₃ | CH₃ | C₂H₅ | C₂H₅ |
| C.297. | tetrahydrofuran-3-yl | CH₃ | CH₃ | C₂H₅ | C₂H₅ |
| C.298. | 6-chloropyridin-3-yl | CH₃ | CH₃ | CH₂—CH₂—CH₂ | |
| C.299. | 6-(trifluoromethyl)pyridin-3-yl | CH₃ | CH₃ | CH₂—CH₂—CH₂ | |
| C.300. | 6-(chlorodifluoromethyl)pyridin-3-yl | CH₃ | CH₃ | CH₂—CH₂—CH₂ | |
| C.301. | 6-(trichloromethyl)pyridin-3-yl | CH₃ | CH₃ | CH₂—CH₂—CH₂ | |
| C.302. | 6-(difluoromethyl)pyridin-3-yl | CH₃ | CH₃ | CH₂—CH₂—CH₂ | |
| C.303. | 6-(1,1-difluoroethyl)pyridin-3-yl | CH₃ | CH₃ | CH₂—CH₂—CH₂ | |
| C.304. | 5,6-dichloropyridin-3-yl | CH₃ | CH₃ | CH₂—CH₂—CH₂ | |

TABLE C.I-continued

| No | Het | R¹ | R² | R³ | R⁴ |
|---|---|---|---|---|---|
| C.305. | 5-(3-fluoro-2-chloropyridyl) | CH₃ | CH₃ | CH₂—CH₂—CH₂ |  |
| C.306. | 5-(2-chlorothiazolyl) | CH₃ | CH₃ | CH₂—CH₂—CH₂ |  |
| C.307. | 5-(2-trifluoromethylthiazolyl) | CH₃ | CH₃ | CH₂—CH₂—CH₂ |  |
| C.308. | 3-tetrahydrofuranyl | CH₃ | CH₃ | CH₂—CH₂—CH₂ |  | in table C.I "#" of Het indicates the bond in formula I;

Further examples of such especially preferred compounds are compounds of formula (I-C), wherein R³, R⁴ and Het have the meanings given in any of lines C.309 to C.396 of table C.II.

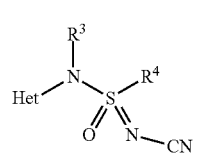

(I-C)

Further examples of such especially preferred compounds are also compounds of formula (I-D), wherein R³, R⁴ and Het have the meanings given in any of lines C.309 to C.396 of table C.II.

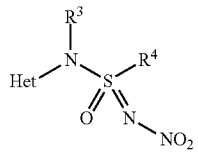

(I-D)

TABLE C.II

| No | Het | R³ | R⁴ |
|---|---|---|---|
| C.309. | 5-(2-chloropyridyl) | H | CH₃ |
| C.310. | 5-(2-trifluoromethylpyridyl) | H | CH₃ |
| C.311. | 5-(2-chlorodifluoromethylpyridyl) | H | CH₃ |
| C.312. | 5-(2-trichloromethylpyridyl) | H | CH₃ |
| C.313. | 5-(2-difluoromethylpyridyl) | H | CH₃ |
| C.314. | 5-(2-(1,1-difluoroethyl)pyridyl) | H | CH₃ |
| C.315. | 5-(2,3-dichloropyridyl) | H | CH₃ |
| C.316. | 5-(3-fluoro-2-chloropyridyl) | H | CH₃ |
| C.317. | 5-(2-chlorothiazolyl) | H | CH₃ |
| C.318. | 5-(2-trifluoromethylthiazolyl) | H | CH₃ |
| C.319. | 3-tetrahydrofuranyl | H | CH₃ |
| C.320. | 5-(2-chloropyridyl) | H | C₂H₅ |
| C.321. | 5-(2-trifluoromethylpyridyl) | H | C₂H₅ |
| C.322. | 5-(2-chlorodifluoromethylpyridyl) | H | C₂H₅ |
| C.323. | 5-(2-trichloromethylpyridyl) | H | C₂H₅ |

TABLE C.II-continued
| No | Het | R³ | R⁴ |
|---|---|---|---|
| C.324. | 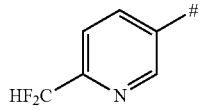 | H | C₂H₅ |
| C.325. | 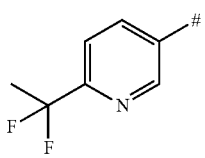 | H | C₂H₅ |
| C.326. | 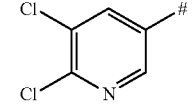 | H | C₂H₅ |
| C.327. | 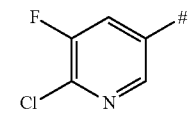 | H | C₂H₅ |
| C.328. | 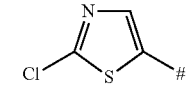 | H | C₂H₅ |
| C.329. | 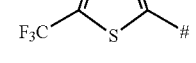 | H | C₂H₅ |
| C.330. | 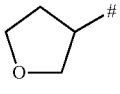 | H | C₂H₅ |
| C.331. | 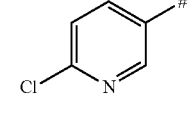 | CH₃ | CH₃ |
| C.332. | 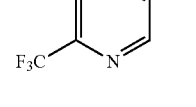 | CH₃ | CH₃ |
| C.333. | 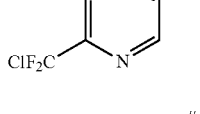 | CH₃ | CH₃ |
| C.334. | 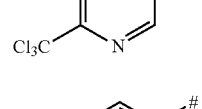 | CH₃ | CH₃ |
| C.335. | 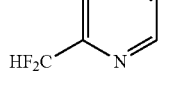 | CH₃ | CH₃ |
| C.336. | 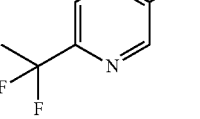 | CH₃ | CH₃ |
| C.337. | 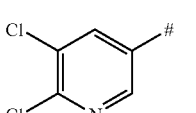 | CH₃ | CH₃ |
| C.338. | 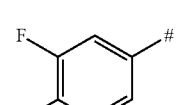 | CH₃ | CH₃ |
| C.339. | 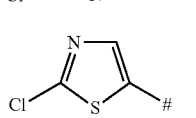 | CH₃ | CH₃ |
| C.340. | 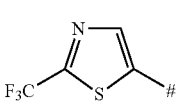 | CH₃ | CH₃ |
| C.341. | 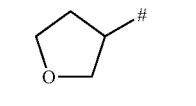 | CH₃ | CH₃ |
| C.342. | 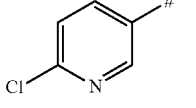 | CH₃ | C₂H₅ |
| C.343. | 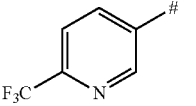 | CH₃ | C₂H₅ |
| C.344. | 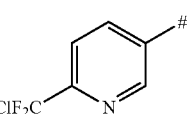 | CH₃ | C₂H₅ |
| C.345. | 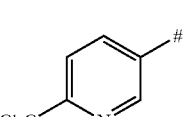 | CH₃ | C₂H₅ |
| C.346. | 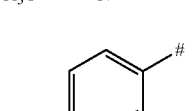 | CH₃ | C₂H₅ |
| C.347. | 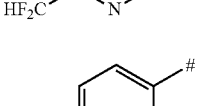 | CH₃ | C₂H₅ |

TABLE C.II-continued
| No | Het | R³ | R⁴ |
|---|---|---|---|
| C.348. | 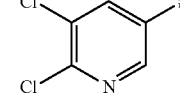 | CH₃ | C₂H₅ |
| C.349. | 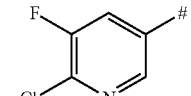 | CH₃ | C₂H₅ |
| C.350. | 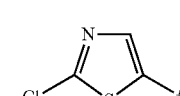 | CH₃ | C₂H₅ |
| C.351. | 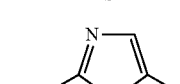 | CH₃ | C₂H₅ |
| C.352. | 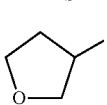 | CH₃ | C₂H₅ |
| C.353. | 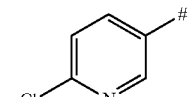 | C₂H₅ | CH₃ |
| C.354. | 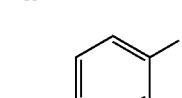 | C₂H₅ | CH₃ |
| C.355. | 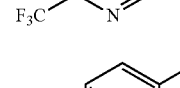 | C₂H₅ | CH₃ |
| C.356. | 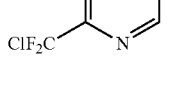 | C₂H₅ | CH₃ |
| C.357. | 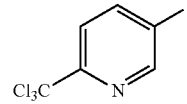 | C₂H₅ | CH₃ |
| C.358. | 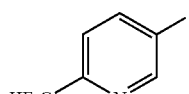 | C₂H₅ | CH₃ |
| C.359. | 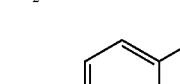 | C₂H₅ | CH₃ |
| C.360. | 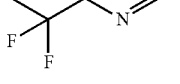 | C₂H₅ | CH₃ |
TABLE C.II-continued
| No | Het | R³ | R⁴ |
|---|---|---|---|
| C.361. | 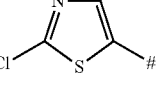 | C₂H₅ | CH₃ |
| C.362. | 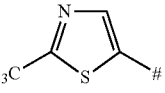 | C₂H₅ | CH₃ |
| C.363. |  | C₂H₅ | CH₃ |
| C.364. | 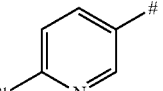 | C₂H₅ | C₂H₅ |
| C.365. | 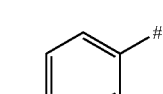 | C₂H₅ | C₂H₅ |
| C.366. | 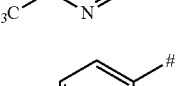 | C₂H₅ | C₂H₅ |
| C.367. | 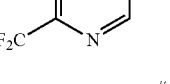 | C₂H₅ | C₂H₅ |
| C.368. | 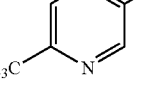 | C₂H₅ | C₂H₅ |
| C.369. | 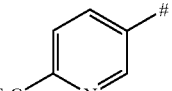 | C₂H₅ | C₂H₅ |
| C.370. | 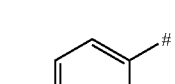 | C₂H₅ | C₂H₅ |
| C.371. | 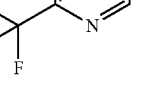 | C₂H₅ | C₂H₅ |
| C.372. | 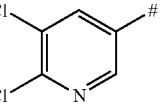 | C₂H₅ | C₂H₅ |
| C.373. | 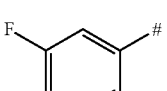 | C₂H₅ | C₂H₅ |

TABLE C.II-continued

| No | Het | R³ | R⁴ |
|---|---|---|---|
| C.374. | tetrahydrofuran-3-yl | C₂H₅ | C₂H₅ |
| C.375. | 6-chloropyridin-3-yl | | CH₂—CH₂—CH₂ |
| C.376. | 6-(trifluoromethyl)pyridin-3-yl | | CH₂—CH₂—CH₂ |
| C.377. | 6-(chlorodifluoromethyl)pyridin-3-yl | | CH₂—CH₂—CH₂ |
| C.378. | 6-(trichloromethyl)pyridin-3-yl | | CH₂—CH₂—CH₂ |
| C.379. | 6-(difluoromethyl)pyridin-3-yl | | CH₂—CH₂—CH₂ |
| C.380. | 6-(1,1-difluoroethyl)pyridin-3-yl | | CH₂—CH₂—CH₂ |
| C.381. | 5,6-dichloropyridin-3-yl | | CH₂—CH₂—CH₂ |
| C.382. | 5-fluoro-6-chloropyridin-3-yl | | CH₂—CH₂—CH₂ |
| C.383. | 2-chlorothiazol-5-yl | | CH₂—CH₂—CH₂ |
| C.384. | 2-(trifluoromethyl)thiazol-5-yl | | CH₂—CH₂—CH₂ |
| C.385. | tetrahydrofuran-3-yl | | CH₂—CH₂—CH₂ |
| C.386. | 6-chloropyridin-3-yl | | CH₂—CH₂—CH₂—CH₂ |
| C.387. | 6-(trifluoromethyl)pyridin-3-yl | | CH₂—CH₂—CH₂—CH₂ |
| C.388. | 6-(chlorodifluoromethyl)pyridin-3-yl | | CH₂—CH₂—CH₂—CH₂ |
| C.389. | 6-(trichloromethyl)pyridin-3-yl | | CH₂—CH₂—CH₂—CH₂ |
| C.390. | 6-(difluoromethyl)pyridin-3-yl | | CH₂—CH₂—CH₂—CH₂ |
| C.391. | 6-(1,1-difluoroethyl)pyridin-3-yl | | CH₂—CH₂—CH₂—CH₂ |
| C.392. | 5,6-dichloropyridin-3-yl | | CH₂—CH₂—CH₂—CH₂ |
| C.393. | 5-fluoro-6-chloropyridin-3-yl | | CH₂—CH₂—CH₂—CH₂ |
| C.394. | 2-chlorothiazol-5-yl | | CH₂—CH₂—CH₂—CH₂ |
| C.395. | 2-(trifluoromethyl)thiazol-5-yl | | CH₂—CH₂—CH₂—CH₂ |
| C.396. | tetrahydrofuran-3-yl | | CH₂—CH₂—CH₂—CH₂ | in table C.II "#" of Het indicates the bond in formula I;

Preparation Methods

Compound of formula (I) according to the present invention can be prepared e.g. according to preparation methods and preparation schemes as described below.

Methods for the Preparation of Sulfoximinamid Compounds of Formula (I):

In the following schemes and methods, if not otherwise specified, the definition of the substituents, variables and indices in the formulae used correspond to the definitions given for formula (I) above.

Scheme A:

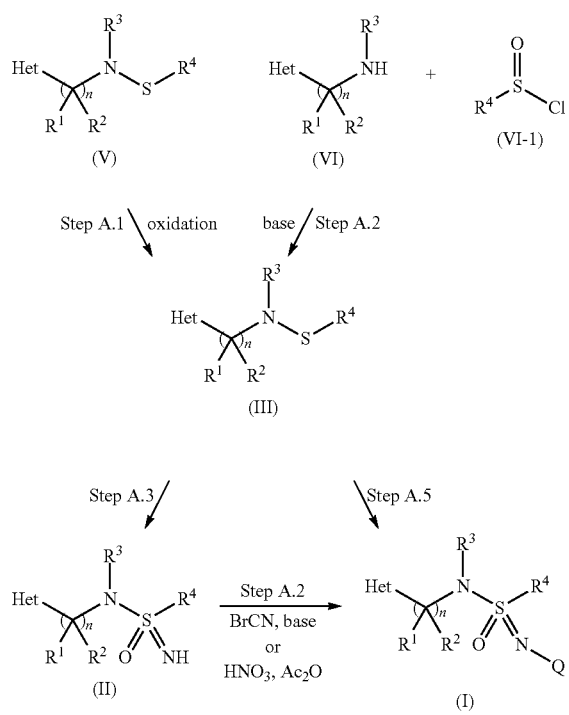

Step A.1: Thus, sulfenamides of formula (V) can be oxidized to the corresponding sulfinamides (III) by treatment with an appropriate oxidant in a suitable solvent. The oxidation is preferably carried out with hydrogen peroxide. Solvents which can be used are water, acetonitrile, carboxylic acids such as acetic acid, trifluoroacetic acid, propionic acid, alcohols such as methanol, ethanol, isopropanol, tert.-butanol, hexafluoroisopropanol, chlorinated hydrocarbons such as methylene chloride, 1,1,2,2-tetrachloroethane, or ketones such as acetone or methyl ethyketone. The reaction can be catalyzed by adding strong acids such as trifluoroacetic acid or perchloroacetic acid. Metal compounds such as vanadium pentoxide, sodium tungstate are also suitable catalysts. Other preferred oxidizing agents are peracids, such as peracetic acid, per-trifluoroacetic acid or 3-chloroperoxybenzoic acid.

Particularly preferred oxidants are hydrogen peroxide in the presence of hexafluoroisopropanol, or 3-chloroperoxybenzoic acid at temperatures below 0° C., or sodium periodate.

Preferred solvents are dichloromethane, chloroform or acetonitrile and include water and alcohols such as methanol or ethanol in cases where sodium periodate is the oxidant.

Step A.2: A different route for the synthesis of sulfinamides (III) makes use of the coupling between amines (VI) and sulfinyl chlorides (VI.1) in the presence of a base in a suitable solvent.

Suitable bases are, in general, inorganic compounds, such as alkali metal and alkaline earth metal oxides, such as lithium oxide, sodium oxide, calcium oxide and magnesium oxide, alkali metal and alkaline earth metal carbonates, such as lithium carbonate, sodium carbonate, potassium carbonate, cesium carbonate and calcium carbonate, and also alkali metal bicarbonates, such as sodium bicarbonate, alkali metal and alkaline earth metal alkoxides, such as sodium methoxide, sodium ethoxide, potassium ethoxide and potassium tert.-butoxide, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to bases such as sodium carbonate, potassium carbonate, caesium carbonate, triethylamine and sodium bicarbonate.

Preferred is the use of tertiary amine bases such as triethyl amine or N,N-diisopropylethyl amine and of solvents such as dichloromethane, chloroform or dimethylformamide.

Step A.3: Sulfinamides of formula (III) can be converted to the corresponding sulfoximinamides (II) by incubation with sodium azide in the presence of concentrated sulfuric acid in an aprotic solvent at elevated temperature as outlined in J. Org. Chem. 1989, 54, 986-988. To avoid the handling of hazardous hydrazoic acid at high temperatures, this transformation may alternatively be achieved at lower temperatures (e.g. 0° C.) using oleum as an acid. Sulfinamides of formula (III) can also be iminated by reaction with O-mesitylsulfonylhydroxylamine (see J. Org. Chem., 39, 16, 1974, 2458-59). Dichloromethane or chloroform are the preferred solvents for these transformations.

Step A.4: N-Nitro- or N-cyano-sulfoximinamides of formula (I) can be obtained from sulfoximinamides (II) by cyanation or nitration of the imine nitrogen atom. For introduction of the cyano group, the sulfoximinamide is incubated with cyanogen bromide in the presence of a base such as N,N-dimethylaminopyridine. Nitration is achieved by reaction of sulfoximinamides (II) with nitric acid in the presence of acetic anhydride and sulfuric acid as a catalyst under mildly elevated temperatures (see Synthesis, 1986, 5, 426-7).

Step A.5: N-cyano-sulfoximinamides of formula (I) can also be obtained by imination of the corresponding sulfinamides (III) by reaction with cyanamid in the presence of a base such as potassium tert. butoxide and a suitable chlorinating agent, such as N-chlorosuccinimide as outlined in Beilstein J. of Org. Chem 2007, 3:25, 1.

Other individual ways in the preparation processes are outlined in the following.

N-Cyanosulfoximinamides of formula (Id), wherein Q represents CN can be prepared by the mild and efficient method illustrated in Scheme B.

Scheme B:

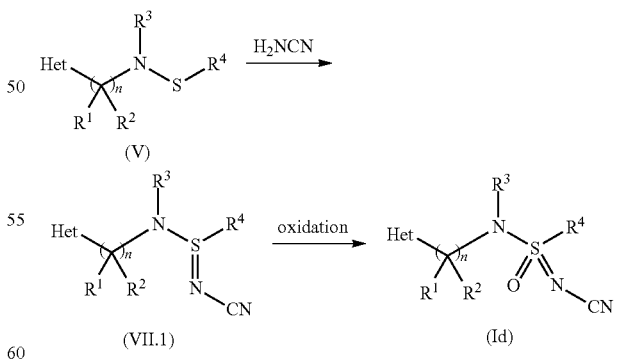

Oxidation of sulfenamides of formula (V) with iodosobenzene diacetate in the presence of cyanamide at 0° C. or ambient temperature provides the corresponding sulfiliminamides (VII.1). This transformation can be carried out in suitable solvents such as dichlorometane or acetonitrile. Conversion of sulfiliminamides (VII.1) to the corresponding sulfoximinamides (Id) can be achieved by oxidation using meta-chloroperbenzoic acid in the presence of a base such as potassium carbonate or potassium bicarbonate. Polar protic solvents such as mixtures of ethanol and water are the preferred solvents, however, dichloromethane may be used if the sulfiliminamide starting material is sufficiently soluble in this solvent.

Sulfoximinamides of formula (II) can also be prepared starting from sulfenamides (V) using alternate routes as illustrated in Schemes C and D.

Scheme C:

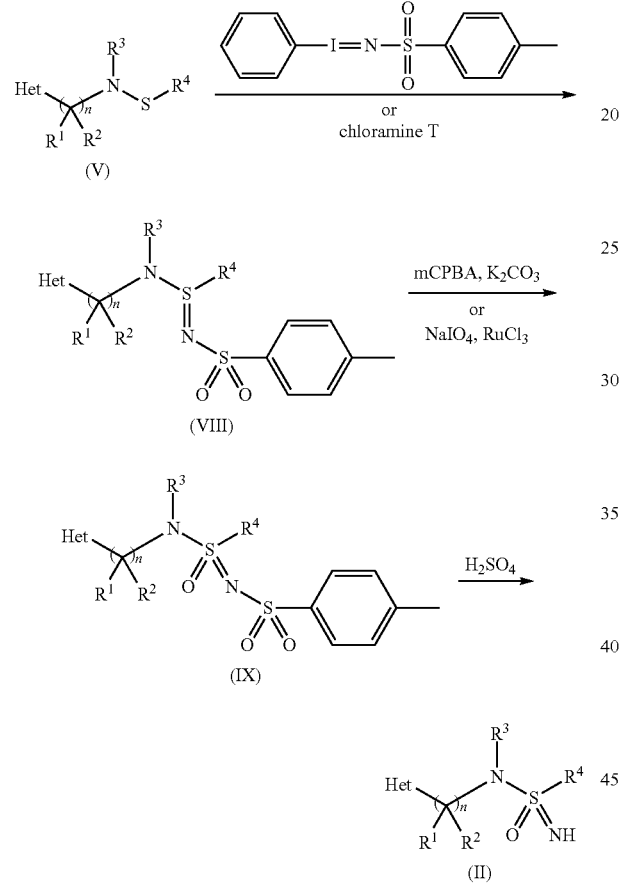

ment of N-tosyl-sulfoximinamides (IX) with concentrated sulfuric acid at ambient temperature.

An additional route for the preparation of sulfoximinamides (II) from sulfenamides (V) is outlined in Scheme D.

Scheme D:

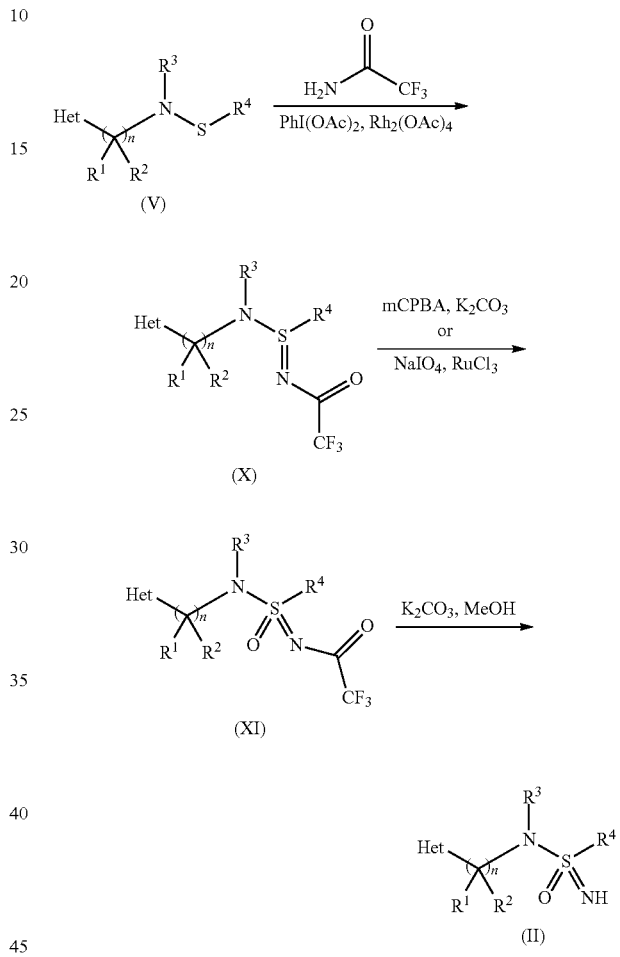

Thus, reaction of sulfenamides (V) with N-chloro-p-toluenesulfonamide (chloramine T) and a base or with 4-methyl-N-(phenylidodinene)-benzenesulfonamide in the presence of catalytic rhodium (II) acetate yields N-tosyl-sulfiliminamides (VIII). Polar aprotic solvents such as dichloromethane or acetonitrile are preferred solvents for this transformation. N-Tosyl-sulfiliminamides (VIII) can be converted to the corresponding N-tosyl-sulfoximinamides (IX) by oxidation with meta-chloroperbenzoic acid (mCPBA) in the presence of a base such as potassium carbonate. Alternatively, sulfoximinamides (IX) can also be prepared using aqueous sodium periodate in the presence of catalytic ruthenium trichloride or a similar catalyst in a suitable solvent such as dichloromethane, chloroform or acetonitrile. Removal of the tosyl group to give sulfoximinamides (II) can be achieved by treat- Reaction of sulfenamides (V) with iodosobenzene diacetate and trifluoroacetamide in the presence of a catalyst such as rhodium diacetate and a base such as magnesium oxide yields N-trifluoroacetyl protected sulfiliminamides (X). The reaction is preferably carried out in a polar aprotic solvent such as dichloromethane. Oxidation of sulfiliminamides of formula (X) with meta-chloroperbenzoic acid in the presence of a base or with aqueous sodium periodate in the presence of a catalyst such as ruthenium trichloride provides N-trifluoroacetyl-protected sulfoximinamides (XI). Incubation of these intermediates with a base in a protic solvent leads to deprotection of the trifluoroacetyl group to give sulfoximinamides (II). Preferred is the use of potassium carbonate as base in solvents such as methanol or ethanol.

The sulfenamide starting materials of formula (V) in Schemes A to D can be prepared using several different routes as illustrated in Scheme E.

Scheme E:

Step E1:

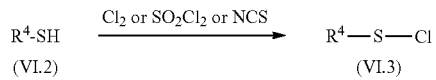

Step E2:

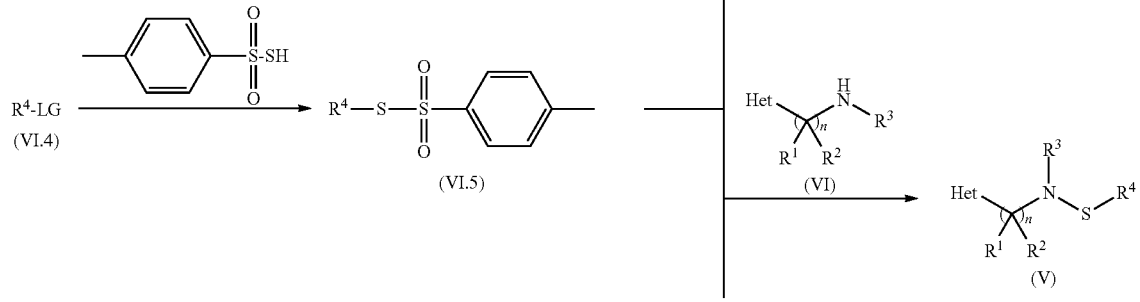

Step E3:

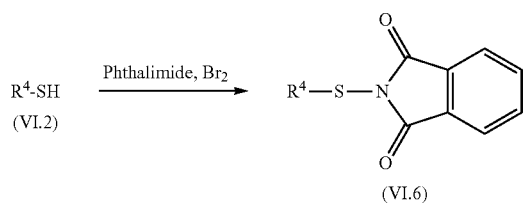

Step E4:

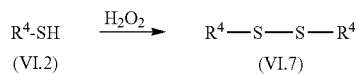

Step E.1 Sulfenyl halogenides of formula (VI.3), obtained by chlorination of mercaptans (VI.2) represent the oldest known sulfenyl transfer reagents (see, for example Chem. Rev. 1989, 89 (4), 689-712). Preferred conditions for the chlorination of thiols include the use of chlorine gas, sulfuryl chloride or N-chlorosuccinimide as chlorinating reagents in an aprotic solvent such as dichloromethane or toluene and the presence of a nitrogen base such as triethylamine or pyridine. Reaction of the resulting sulfenyl halogenides with amines (VI) in the presence of an amine base to scavenge the liberated hydrochloric acid in a polar aprotic solvent yields the desired sulfenamides (V).

Step E.2: Sulfenamides (V) are also accessible starting from thiolsulfonates (VI.5) by reaction with amines (VI) as described in J. Org. Chem. 1977, 31, 2842-2846. The thiolsulfonate intermediates are readily available by S-alkylation of thiosulfonic acids (or the salts thereof) using an appropriate alkylating agent $R^4$-LG (VI.4), wherein LG denotes a leaving group such as halide, triflate, etc., in the presence of a base.

Step E.3: Thus, sulfenimides (VI.6), prepared from mercaptans (VI.2) and phthalimide according to the conditions outlined in Tetrahedron 1997, 53 (42), 14411-14416, can also be reacted with amines (VI) at ambient or elevated temperature to furnish sulfenamides (V) as described in Tetrahedron Lett. 1971, 52, 4953-4956. Aprotic solvents such as dichloromethane or toluene are preferred for this transformation.

Step E.4: Metal ion-assisted cleavage of disulfides (VI.7) and subsequent reaction with amines (VI) represents an additional route to sulfenamides (V) (see, for example J. Org. Chem. 1977, 42, 967-972) starting from mercaptanes (VI.2). Preferred is the use of monovalent silver-I and bivalent mercury-II salts such as silver nitrate, silver acetate or mercuric chloride.

Cyclic sulfenamides of formula (XIII), wherein $R^3$ and $R^4$ form a saturated 5- or 6-membered ring, meaning r is equal 1 or 2, can also be prepared as outlined in Scheme F.

Scheme F:

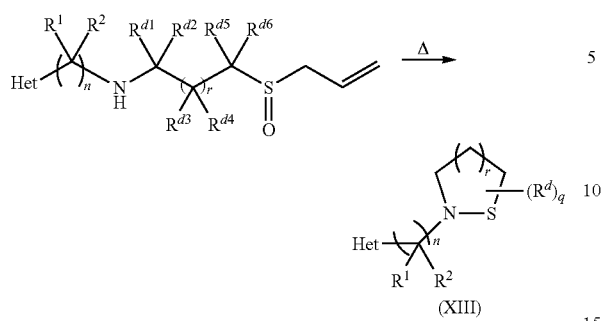

Thus, elevated temperatures enable Mislow-Evans rearrangement of allyl sulfoxide (XII), followed by attack of the amine nitrogen atom onto the transiently generated allyl sulfenate leading to intramolecular ring closure to the corresponding cyclic sulfenamide (XIII) as described in Heterocycles 1985, 23 (8), 1897-1900. This transformation is preferably carried out in aprotic solvents such as cyclohexane or ethyl acetate. Allyl sulfoxide intermediates (XII) can be derived from acrolein as outlined in the literature reference cited above or obtained from different starting materials by standard synthetic methods known to those skilled in the art. In scheme F, $R^{d1}$-$R^{d6}$ are selected independently from one another and independently from r and correspond to $R^d$ as previously defined, and q may represent an integer selected from 0, 1 or 2.

Cyclic sulfenamides of formula (XVI), wherein $R^3$ and $R^4$ form a saturated 5-membered ring, can also be obtained starting from a thietane derivative (XIV) as described in Scheme G.

Scheme G:

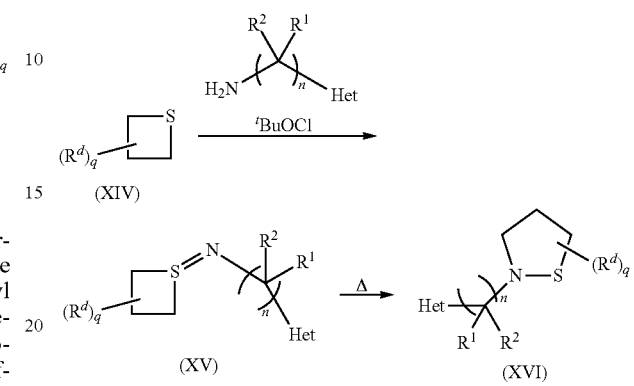

Thus, reaction of a thietane of formula (XIV) with tert-butylypochloride in the presence of a primary amine yields sulfilimines of formula (XV) as described in Monatshefte für Chemie 1985, 116 (10), 1153-1164. These sulfilimines (XV) rearrange at ambient or elevated temperature to give the corresponding thiazolidines (XVI). Preferred solvent for this transformation is chloroform.

Scheme H:

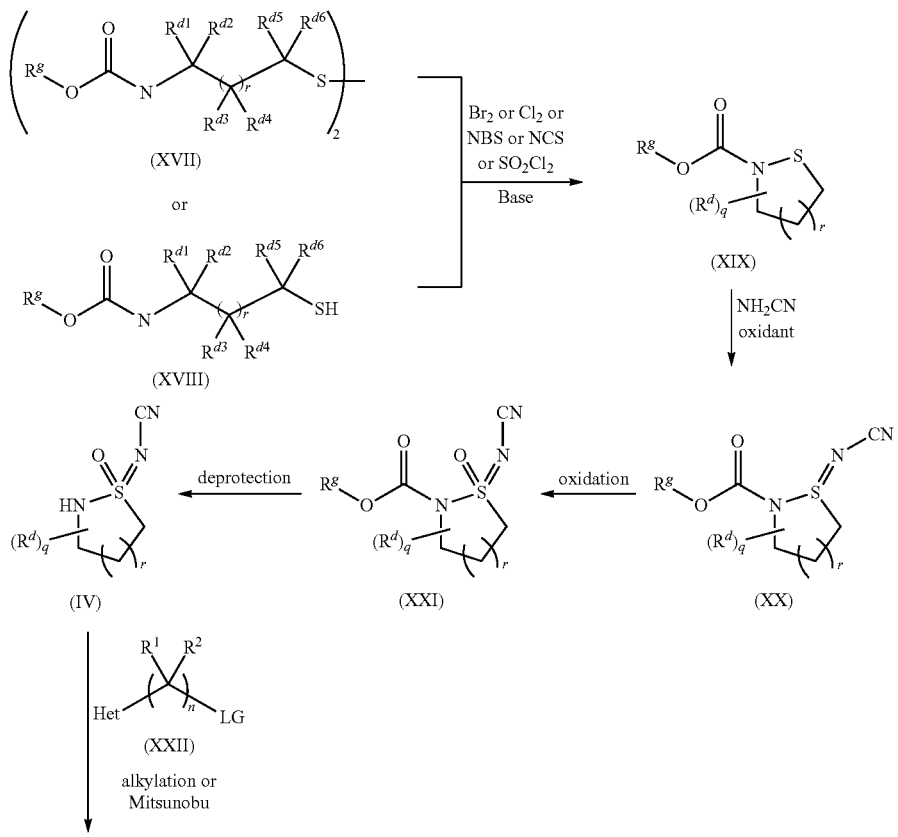

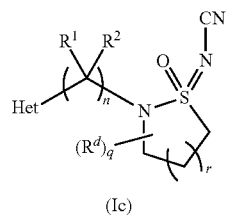

(Ic)

Cyclic sulfoximinamides of formula (Ic), wherein $R^3$ and $R^4$ form a saturated 5- or 6-membered ring, i.e. r is equal to 1 or 2, q represents an integer selected from 0, 1, or 2 and $R^d$ is as previously defined can also be prepared as outlined in Scheme H, wherein $R^{d1}$-$R^{d6}$ are selected independently from one another and independently from r and correspond to $R^d$ as previously defined and $R^9$ is $C_1$-$C_4$-alkyl, wherein the carbon atoms may carry any combination of 1 or 2 radicals selected from phenyl, $C_1$-$C_4$-alkyl, $C_1$-$C_4$-haloalkyl, or $C_2$-$C_6$-alkenyl.

Thus, carbamoyl-protected aminodisulfides (XVII) or aminomercaptans (XVIII) can be converted to cyclic sulfenamides (XIX) by incubation with a reagent such as $Br_2$, $Cl_2$, NBS, NCS or $SO_2Cl_2$ in the presence of a base such as pyridine. Preferably, this transformation is carried out in an aprotic solvent such as dichloromethane or toluene. Sulfiliminamides (XX) can be obtained from sulfenamides (XIX) by reaction with cyanamide or sodium cyanamide in the presence of an oxidant such as iodosobenzene diacetate or tert-butyl hypochloride. This transformation is carried out in suitable solvents such as dichlorometane or acetonitrile.

Conversion of sulfiliminamides (XX) to the corresponding carbamoyl-protected sulfoximinamides (XXI) can be achieved by oxidation using for example aqueous NaOCl or tert-butyl hypochloride as oxidizing agents. This transformation is preferably carried out in a biphasic mixture of $H_2O$ and a chlorinated solvent such as dichloromethane and in the presence of a phase transfer catalyst such as tetrabutylammonium bromide. Depending on the nature of the residue $R^a$, carbamate-deprotection to yield cyclic sulfoximinamides (IV) can be achieved by methods suitable for the corresponding protecting group, as detailed for example in T. M. Greene, P. G. M. Wuts, Protecting Groups in Organic Chemistry, 3rd ed., John Wiley & Sons, New York 1999.

Sulfoximinamides of formula (Ic) are accessible from unprotected sulfoximinamides (IV) by alkylation with a suitable analog (XXII), for which LG denotes an appropriate leaving group (e.g. halide) in the presence of a base in a polar aprotic solvent. Preferably this transformation is carried out under Mitsunobu-conditions with (XXII) being an alcohol derivative (LG=OH), as detailed in O. Mitsunobu, Y. Yamada, Bull. Chem. Soc. Japan 1967, 40, 2380-2382.

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Pests

The compounds of the formula I, and their salts are in particular suitable for efficiently controlling arthropodal pests such as arachnids, myriapedes and insects as well as nematodes.

The compounds of the formula I are especially suitable for efficiently combating the following pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippoc-* astani, *Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Rticulitermes santonensis, Reticulitermes grassei, Termes natalensis,* and *Coptotermes formosanus;* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla pin, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the formula I and their salts are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis.*

Compounds of the formula I are particularly useful for controlling insects, preferably sucking or piercing insects such as insects from the genera Thysanoptera, Diptera and Hemiptera, in particular the following species:

Thysanoptera: *Frankliniella fusca, Frankliniella occidentalis, Frankliniella tritici, Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand,* and *Viteus vitifolii;*

Compounds of the formula I are particularly useful for controlling insects of the orders Hemiptera and Thysanoptera.

Formulations

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-methyl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.
carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal Suitable thickeners are compounds which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from R.T. Vanderbilt), or organic phyllosilicates, such as Atta-clay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nut-shell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:
1. Products for dilution with water. For seed treatment purposes, such products may be applied to the seed diluted or undiluted.

A) Water-Soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-ethyl, azinphos-methyl, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide; (R)-, (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid (M21.1)

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, 4-But-2-ynyloxy-6-(3,5-dimethyl-piperidin-1-yl)-2-fluoro-pyrimidine (M22.1), 3-Benzoylamino-N-[2,6-dimethyl-4-(1,2,2,2-tetrafluoro-1-trifluoromethyl-ethyl)-phenyl]-2-fluoro-benzamide (M22.2), 4-[5-(3,5-Dichloro-phenyl)-5-trifluoromethyl-4,5-dihydro-isoxazol-3-yl]-2-methyl-N-pyridin-2-ylmethyl-benzamide (M22.3), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.4), 4-[5-(3,5-Dichloro-phenyl)-5-trifluoromethyl-4,5-dihydro-isoxazol-3-yl]-2-methyl-N-thiazol-2-ylmethyl-benzamide (M22.5), 4-[5-(3,5-Dichloro-phenyl)-5-trifluoromethyl-4,5-dihydro-isoxazol-3-yl]-2-methyl-N-(tetrahydro-furan-2-ylmethyl)-benzamide (M22.6), 4-{[(6-Bromopyrid-3-yl)methyl](2-fluoroethyl)amino}furan-2(5H)-on (M22.7), 4-{[(6-Fluoropyrid-3-yl)methyl](2,2-difluoroethyl)amino}furan-2(5H)-on (M22.8), 4-{[(2-Chloro1,3-thiazolo-5-yl)methyl](2-fluoroethyl)amino}furan-2(5H)-on (M22.9), 4-{[(6-Chloropyrid-3-yl)methyl](2-fluoroethyl)amino}furan-2(5H)-on (M22.10), 4-{[(6-Chloropyrid-3-yl)methyl](2,2-difluoroethyl)amino}furan-2(5H)-on (M22.11), 4-{[(6-Chloro-5-fluoropyrid-3-yl)methyl](methyl)amino}furan-2(5H)-on (M22.12), 4-{[(5,6-Dichloropyrid-3-yl)methyl](2-fluoroethyl)amino}furan-2(5H)-on (M22.13), 4-{[(6-Chloro-5-fluoropyrid-3-yl)methyl](cyclopropyl)amino}furan-2(5H)-on (M22.14), 4-{[(6-Chloropyrid-3-yl)methyl](cyclopropyl)amino}furan-2(5H)-on (M22.15), 4-{[(6-Chloropyrid-3-yl)methyl](methyl)amino}furan-2(5H)-on (M22.16), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-[2-hydroxy-4,6a,12b-trimethyl-[1-oxo-9-(3-pyridinyl)-2H,11H-naphtho[2,1-b]pyrano[3,4-e]pyran-3,6-diyl]ester (M22.17), 8-(2-Cyclopropylmethoxy-4-methyl-phenoxy)-3-(6-methyl-pyridazin-3-yl)-3-aza-bicyclo[3.2.1]octane (M22.18), M.23. N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl;

M.24. Anthranilamides: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M24.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M24.2), 5-Bromo-2-(3-chloro-pyridin-2-yl)-2H-pyrazole-3-carboxylic acid [2-bromo-4-cyano-6-

(1-cyclopropyl-ethylcarbamoyl)-phenyl]-amide (M24.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M24.4), 5-Bromo-2-(3-chloro-pyridin-2-yl)-2H-pyrazole-3-carboxylic acid [2,4-dichloro-6-(1-cyclopropyl-ethylcarbamoyl)-phenyl] amide (M24.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M24.6), M.25. Malononitrile compounds: $CF_2HCF_2CF_2CF_2CH_2C(CN)_2CH_2CH_2CF_3$, (2-(2,2,3,3,4,4,5,5-octafluoropentyl)-2-(3,3,3-trifluoro-propyl)malononitrile), $CF_2HCF_2CF_2CF_2CH_2C(CN)_2CH_2CH_2CF_2CF_3$ (2-(2,2,3,3,4,4,5,5-octafluoropentyl)-2-(3,3,4,4,4-pentafluorobutyl)-malonodinitrile);

M.26. Microbial disruptors: *Bacillus thuringiensis* subsp. *lsraelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

The commercially available compounds of the group M may be found in The Pesticide Manual, 13th Edition, British Crop Protection Council (2003) among other publications.

Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Cyantraniliprole has been described in WO 01/70671, WO 04/067528 and WO 05/118552. The anthranilamides M 24.1 to M 24.6 have been described in WO 2008/72743 and WO 200872783. The phthalamide M 21.1 is known from WO 2007/101540. Cyflumetofen and its preparation have been described in WO 04/080180. The aminoquinazolinone compound pyrifluquinazon has been described in EPA 109 7932. Sulfoximine sulfoxaflor has been described in WO 2006/060029 and WO 2007/149134. The alkynylether compound M22.1 is described e.g. in JP 2006131529. Organic sulfur compounds have been described in WO 2007060839. The carboxamide compound M 22.2 is known from WO 2007/83394. The oxazoline compounds M 22.3 to M 22.6 have been described in WO 2007/074789. The furanon compounds M 22.7 to M 22.16 have been described eg. in WO 2007/115644. The pyripyropene derivative M 22.17 has been described in WO 2008/66153 and WO 2008/108491. The pyridazin compound M 22.18 has been described in JP 2008/115155. The malononitrile compounds have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoxim-methyl, metominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

Applications

The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5):1225-35., Curr Opin Chem Biol. 2006 October; 10(5):487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resuiting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)

G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a Gelling Agent is Carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or the enantiomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
   Solutions such as oral solutions, concentrates for oral administration after dilution, solutions for use on the skin or in body cavities, pouring-on formulations, gels;
   Emulsions and suspensions for oral or dermal administration; semi-solid preparations;
   Formulations in which the active compound is processed in an ointment base or in an oil-in-water or water-in-oil emulsion base;
   Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ecto-parasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The present invention is now illustrated in further details by the following examples.

EXAMPLES

The present invention is now illustrated in further details by the following examples.

Examples of compounds of formula I according to the present invention are given in tables E.1, E.2 and E.3 below.

TABLE E.1
Examples of compounds according to formula I-E:
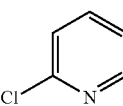
formula (I-E)
| No | Het | n | m | R¹ | R² | r | R$^{a1}$ | R$^{a2}$ | R$^{b1}$ | R$^{b2}$ |
|---|---|---|---|---|---|---|---|---|---|---|
| 1 | 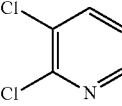 | 1 | 1 | H | H | 1 | H | H | H | H |
| 2 | 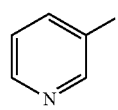 | 1 | 1 | H | H | 1 | H | H | H | H |
| 3 | 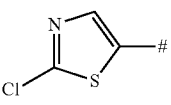 | 1 | 1 | H | H | 1 | H | H | H | H |
| 4 | 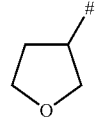 | 1 | 1 | H | H | 1 | H | H | H | H |
| 5 | 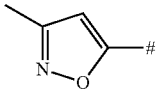 | 1 | 1 | H | H | 1 | H | H | H | H |
| 6 | 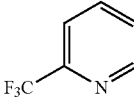 | 1 | 1 | H | H | 1 | H | H | H | H |
| 7 | 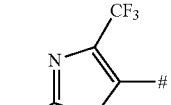 | 1 | 1 | H | H | 1 | H | H | H | H |
| 8 | 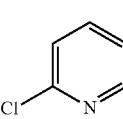 | 1 | 1 | H | H | 1 | H | H | H | H |
| 9 | 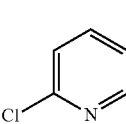 | 1 | 1 | CH$_3$ | H | 1 | H | H | H | H |
| 10 | 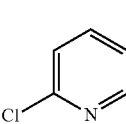 | 1 | 1 | H | H | 2 | H | H | H | H |

TABLE E.1-continued
Examples of compounds according to formula I-E:
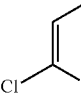
formula (I-E)
| No | Het | n | m | R¹ | R² | r | R$^{a1}$ | R$^{a2}$ | R$^{b1}$ | R$^{b2}$ |
|---|---|---|---|---|---|---|---|---|---|---|
| 11 | 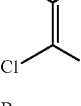 | 0 | 1 | — | — | 1 | H | H | H | H |
| 12 | 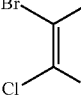 | 0 | 1 | — | — | 1 | H | H | H | H |
| 13 | 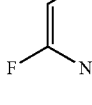 | 0 | 1 | — | — | 1 | H | H | H | H |
| 14 | 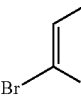 | 0 | 1 | — | — | 1 | H | H | H | H |
| 15 | 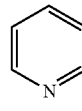 | 0 | 1 | — | — | 1 | H | H | H | H |
| 16 | 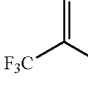 | 0 | 1 | — | — | 1 | H | H | H | H |
| 17 | 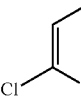 | 0 | 1 | — | — | 1 | H | H | H | H |
| 18 | 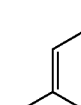 | 0 | 1 | — | — | 1 | H | H | H | H |
| 19 | 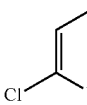 | 0 | 1 | — | — | 1 | H | H | H | H |
| 20 |  | 0 | 1 | — | — | 1 | H | H | H | H |

TABLE E.1-continued
Examples of compounds according to formula I-E:
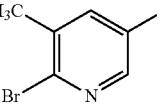
formula (I-E)
| No | Het | n | m | R¹ | R² | r | R$^{a1}$ | R$^{a2}$ | R$^{b1}$ | R$^{b2}$ |
|---|---|---|---|---|---|---|---|---|---|---|
| 21 | 3-H₃C, 2-Br-pyridin-5-yl # | 0 | 1 | — | — | 1 | H | H | H | H |
| 22 | 4-CF₃-pyridin-3-yl # | 0 | 1 | — | — | 1 | H | H | H | H |
| 23 | pyrazin-2-yl # | 0 | 1 | — | — | 1 | H | H | H | H |
| 24 | 5-Cl-pyrazin-2-yl # | 0 | 1 | — | — | 1 | H | H | H | H |
| 25 | 5-Br-pyrazin-2-yl # | 0 | 1 | — | — | 1 | H | H | H | H |
| 26 | pyrimidin-5-yl # | 0 | 1 | — | — | 1 | H | H | H | H |
| 27 | quinolin-3-yl # | 0 | 1 | — | — | 1 | H | H | H | H |
| 28 | tetrahydrofuran-3-yl # | 0 | 1 | — | — | 1 | H | H | H | H |
| 29 | 6-Cl-pyridin-3-yl # | 0 | 1 | — | — | 2 | H | H | H | H |
| 30 | 6-Cl-pyridin-3-yl # | 0 | 1 | — | — | 1 | CH₃ | H | H | H |

TABLE E.1-continued
Examples of compounds according to formula I-E:
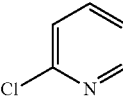
formula (I-E)
| No | Het | n | m | $R^1$ | $R^2$ | r | $R^{a1}$ | $R^{a2}$ | $R^{b1}$ | $R^{b2}$ |
|---|---|---|---|---|---|---|---|---|---|---|
| 31 | 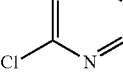 | 0 | 1 | — | — | 1 | Br | H | H | H |
| 32 | 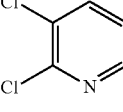 | 0 | 1 | — | — | 1 | H | H | CH₃ | H |
| 33 | 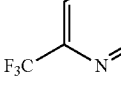 | 0 | 1 | — | — | 1 | H | H | CH₃ | H |
| 34 | 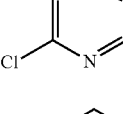 | 0 | 1 | — | — | 1 | H | H | CH₃ | H |
| 35 | 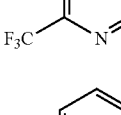 | 0 | 1 | — | — | 1 | H | H | CH₃ | CH₃ |
| 36 | 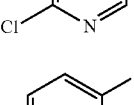 | 0 | 1 | — | — | 1 | H | H | CH₃ | CH₃ |
| 37 | 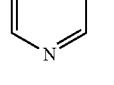 | 1 | 0 | H | H | 1 | H | H | H | H |
| 38 | 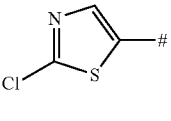 | 1 | 0 | H | H | 1 | H | H | H | H |
| 39 | 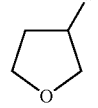 | 1 | 0 | H | H | 1 | H | H | H | H |
| 40 |  | 1 | 0 | H | H | 1 | H | H | H | H |

TABLE E.1-continued
Examples of compounds according to formula I-E:
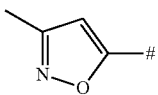
formula (I-E)
| No | Het | n | m | R¹ | R² | r | R$^{a1}$ | R$^{a2}$ | R$^{b1}$ | R$^{b2}$ |
|---|---|---|---|---|---|---|---|---|---|---|
| 41 | 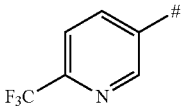 | 1 | 0 | H | H | 1 | H | H | H | H |
| 42 | 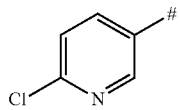 | 1 | 0 | H | H | 1 | H | H | H | H |
| 43 | 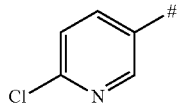 | 1 | 0 | H | H | 2 | H | H | H | H |
| 44 | 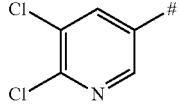 | 0 | 0 | — | — | 1 | H | H | H | H |
| 45 | 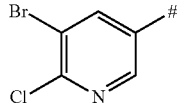 | 0 | 0 | — | — | 1 | H | H | H | H |
| 46 | 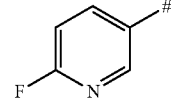 | 0 | 0 | — | — | 1 | H | H | H | H |
| 47 | 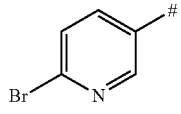 | 0 | 0 | — | — | 1 | H | H | H | H |
| 48 | 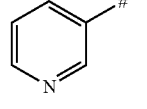 | 0 | 0 | — | — | 1 | H | H | H | H |
| 49 | 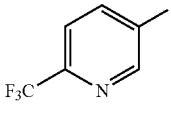 | 0 | 0 | — | — | 1 | H | H | H | H |
| 50 |  | 0 | 0 | — | — | 1 | H | H | H | H |

TABLE E.1-continued
Examples of compounds according to formula I-E:
formula (I-E)
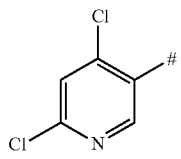
| No | Het | n | m | R¹ | R² | r | $R^{a1}$ | $R^{a2}$ | $R^{b1}$ | $R^{b2}$ |
|---|---|---|---|---|---|---|---|---|---|---|
| 51 | 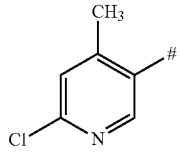 | 0 | 0 | — | — | 1 | H | H | H | H |
| 52 | 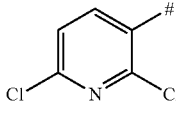 | 0 | 0 | — | — | 1 | H | H | H | H |
| 53 | 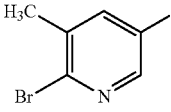 | 0 | 0 | — | — | 1 | H | H | H | H |
| 54 | 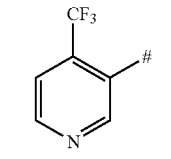 | 0 | 0 | — | — | 1 | H | H | H | H |
| 55 | 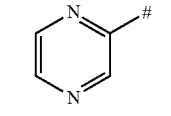 | 0 | 0 | — | — | 1 | H | H | H | H |
| 56 | 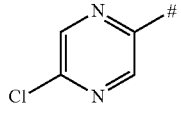 | 0 | 0 | — | — | 1 | H | H | H | H |
| 57 | 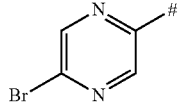 | 0 | 0 | — | — | 1 | H | H | H | H |
| 58 | 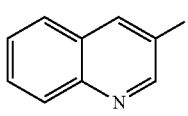 | 0 | 0 | — | — | 1 | H | H | H | H |
| 59 |  | 0 | 0 | — | — | 1 | H | H | H | H |

TABLE E.1-continued
Examples of compounds according to formula I-E:
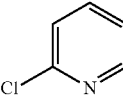
formula (I-E)
| No | Het | n | m | R¹ | R² | r | $R^{a1}$ | $R^{a2}$ | $R^{b1}$ | $R^{b2}$ |
|---|---|---|---|---|---|---|---|---|---|---|
| 60 | 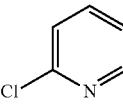 | 0 | 0 | — | — | 2 | H | H | H | H |
| 61 | 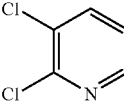 | 0 | 0 | — | — | 1 | H | H | CH₃ | H |
| 62 | 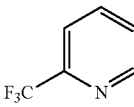 | 0 | 0 | — | — | 1 | H | H | CH₃ | H |
| 63 | 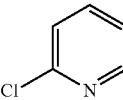 | 0 | 0 | — | — | 1 | H | H | CH₃ | H |
| 64 | 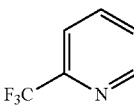 | 0 | 0 | — | — | 1 | H | H | CH₃ | CH₃ |
| 65 | 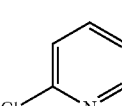 | 0 | 0 | — | — | 1 | H | H | CH₃ | CH₃ |
| 66 | 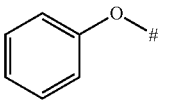 | 0 | 0 | — | — | 1 | H | H | C₆H₅O— | H |

TABLE E.2
Examples of compounds according to formula I-F:
formula (I-F)
| No. | Het | n | m | R¹ | R² | R³ | R⁴ |
|---|---|---|---|---|---|---|---|
| 67 |  | 1 | 1 | CH₃ | H | CH₃ | CH₃ |
| 68 |  | 1 | 1 | CH₃ | H | 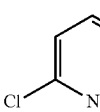 | CH₃ |
| 69 |  | 1 | 1 |  | H | CH₃ | CH₃ |
| 70 |  | 1 | 1 | CH₃ | H | 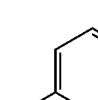 | CH₃ |
| 71 |  | 1 | 1 | 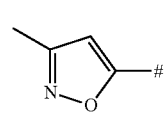 | H | CH₃ | CH₃ |
| 72 |  | 1 | 1 | H | H | CH₃ | CH₃ |
| 73 | 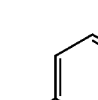 | 1 | 0 | CH₃ | H | CH₃ | CH₃ |
| 74 |  | 1 | 0 | CH₃ | H |  | CH₃ |
| 75 |  | 1 | 0 |  | H | CH₃ | CH₃ |
| 76 |  | 1 | 0 | CH₃ | H |  | CH₃ |
| 77 |  | 1 | 0 | H |  | CH₃ | CH₃ |

TABLE E.2-continued

Examples of compounds according to formula I-F:

formula (I-F)

| No. | Het | n | m | R¹ | R² | R³ | R⁴ |
|---|---|---|---|---|---|---|---|
| 78 | 3-methylisoxazol-5-yl | 1 | 0 | H | H | CH₃ | CH₃ |
| 79 | 6-(trifluoromethyl)pyridin-3-yl | 1 | 1 | H | H | C₂H₅ | CH₃ |
| 80 | 6-chloropyridin-3-yl | 1 | 1 | H | H | cyclopropyl | CH₃ |
| 81 | 6-chloropyridin-3-yl | 0 | 1 | — | — | H | CH₃ |
| 82 | 6-chloropyridin-3-yl | 1 | 1 | H | H | CH₃ | cyclopropyl |
| 83 | 6-chloropyridin-3-yl | 1 | 1 | H | H | cyclopropylmethyl | CH₃ |
| 84 | 6-chloropyridin-3-yl | 1 | 1 | H | H | CH₃ | C₂H₅ |
| 85 | 6-(trifluoromethyl)pyridin-3-yl | 1 | 1 | H | H | CH₃ | CH₃ |
| 86 | 2-chlorothiazol-5-yl | 1 | 1 | H | H | CH₃ | CH₃ |
| 87 | 6-chloropyridazin-3-yl | 1 | 1 | H | H | cyclopropylmethyl | C₂H₅ |
| 88 | 6-chloropyridin-3-yl | 1 | 1 | H | H | C₂H₅ | cyclopropyl |

TABLE E.2-continued
Examples of compounds according to formula I-F:
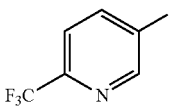
formula (I-F)
| No. | Het | n | m | R¹ | R² | R³ | R⁴ |
|---|---|---|---|---|---|---|---|
| 89 |  | 1 | 1 | H | H | 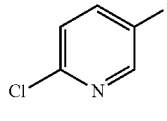 | CH₃ |
| 90 | 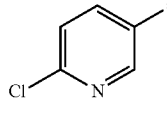 | 1 | 1 | H | H | H | CH₃ |
| 91 | 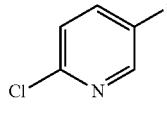 | 1 | 1 | H | H | CH₃ | CH₃ |
| 92 | 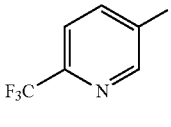 | 1 | 1 | H | H | C₂H₅ | CH₃ |
| 93 | 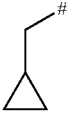 | 1 | 1 | H | H | 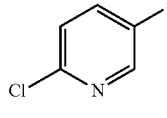 | CH₃ |
| 94 | 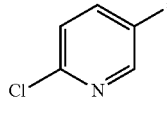 | 1 | 1 | H | H | C₂H₅ | C₂H₅ |
| 95 |  | 1 | 1 | H | H | 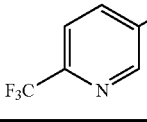 | C₂H₅ |
| 96 |  | 0 | 1 | — | — | H | CH₃ |

TABLE E.3

Examples of compounds according to formula I-G:

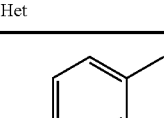

formula (I-G)

| No. | Het | n | m | R¹ | R² | R³ | R⁴ |
|---|---|---|---|---|---|---|---|
| 97 | (6-chloropyridin-3-yl) | # | 1 | 1 | H | H | CH₃ | CH₃ |

The Compound examples can be characterized e.g. by coupled High Performance Liquid Chromatography/mass spectrometry (HPLC/MS), by $^1$H-NMR and/or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

$^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

TABLE E

Physico-chemical data of the compound examples given above in tables E.1, E.2 and E.3

| Compound No. | Physico-chemical data as melting point [° C.], retention time $t_r$ [min], m/z (HPLC/MS) or $^1$H-NMR (CDCl₃) [δ ppm] |
|---|---|
| 1 | $t_r$ = 1.77 min<br>m/z = 271 |
| 2 | $t_r$ = 2.46 min<br>m/z = 305 |
| 3 | $t_r$ = 0.74 min<br>m/z = 237 |
| 4 | $^1$H-NMR: 7.58 (s), 4.58 (s), 3.63-3.77 (m), 3.47 (mc), 2.52 (mc) |
| 5 | $t_r$ = 1.37 min<br>m/z = 230 |
| 6 | $^1$H-NMR: 6.27 (s), 4.52 (d), 4.44 (d), 3.70 (mc), 3.57 (mc), 2.56 (mc), 2.31 (s) |
| 7 | $^1$H-NMR: 8.74 (s), 8.02 (d), 7.60 (d), 4.51 (d), 4.48 (d), 3.76 (mc), 3.61 (mc), 3.41 (mc), 2.55 (mc) |
| 8 | $t_r$ = 2.50 min<br>m/z = 345 |
| 9 | $t_r$ = 2.12 min<br>m/z = 285 |
| 10 | $^1$H-NMR: 8.35 (d), 7.79 (dd), 7.39 (d), 4.46 (d), 4.37 (d), 3.67 (mc), 3.60 (mc), 3.20 (mc), 2.34 (mc), 1.78 (mc) |
| 11 | $t_r$ = 1.84 min<br>m/z = 257 |
| 12 | $t_r$ = 2.45 min<br>m/z = 293 |
| 13 | $t_r$ = 2.50 min<br>m/z = 336 |
| 14 | $t_r$ = 1.67 min<br>m/z = 241 |
| 15 | m.p. = 147° C.<br>$t_r$ = 1.89 min<br>m/z = 301 |
| 16 | m.p. = 96° C.<br>$t_r$ = 0.85 min<br>m/z = 223 |
| 17 | $t_r$ = 2.32 min<br>m/z = 291 |
| 18 | $t_r$ = 2.24 min<br>m/z = 292 |
| 19 | $t_r$ = 2.08 min<br>m/z = 271 |
| 20 | $t_r$ = 2.11 min<br>m/z = 292 |
| 21 | $t_r$ = 2.13 min<br>m/z = 315 |
| 22 | $t_r$ = 1.81 min<br>m/z = 291 |
| 23 | $t_r$ = 1.27 min<br>m/z = 224 |
| 24 | $t_r$ = 2.24 min<br>m/z = 258 |
| 25 | $t_r$ = 1.79 min<br>m/z = 303 |
| 26 | $^1$H-NMR: 9.18 (s), 8.82 (s), 4.12 (mc), 3.92-4.03 (m), 3.75 (mc), 2.80 (mc) |
| 27 | $t_r$ = 1.93 min<br>m/z = 273 |
| 28 | $t_r$ = 1.06 min<br>m/z = 216 |
| 29 | m.p. = 135° C.<br>$t_r$ = 2.03 min<br>m/z = 271 |
| 30 | $t_r$ = 2.10 min<br>m/z = 271 |
| 31 | $t_r$ = 2.26 min<br>m/z = 336 |
| 32 | m.p. = 125° C.<br>$t_r$ = 2.18 min<br>m/z = 271 |
| 33 | $t_r$ = 2.52 min<br>m/z = 306 |
| 34 | $t_r$ = 2.45 min<br>m/z = 305 |
| 35 | m.p. = 90° C.<br>$t_r$ = 2.40 min<br>m/z = 285 |
| 36 | $t_r$ = 2.75 min<br>m/z = 319 |
| 37 | $t_r$ = 1.57 min<br>m/z = 255 |
| 38 | $t_r$ = 0.57 min<br>m/z = 221 |
| 39 | $t_r$ = 1.74 min<br>m/z = 261 |
| 40 | $t_r$ = 1.24 min<br>m/z = 214 |
| 41 | $^1$H-NMR: 6.31 (s), 4.57 (d), 4.40 (d), 3.68 (mc), 3.44 (mc), 2.36 (mc), 2.33 (s) |
| 42 | $t_r$ = 1.98 min<br>m/z = 289 |
| 43 | $^1$H-NMR: 8.36 (d), 7.68 (dd), 7.38 (d), 4.33 (d), 3.97 (d), 3.52 (mc), 3.13 (mc), 2.99 (mc), 2.72 (mc), 2.58 (mc), 1.89 (mc), 1.73 (mc) |
| 44 | $t_r$ = 1.64 min<br>m/z = 241 |

TABLE E-continued

Physico-chemical data of the compound examples given above in tables E.1, E.2 and E.3

| Compound No. | Physico-chemical data as melting point [° C.], retention time $t_r$ [min], m/z (HPLC/MS) or $^1$H-NMR (CDCl$_3$) [δ ppm] |
|---|---|
| 45 | $t_r$ = 2.17 min; m/z = 275 |
| 46 | $t_r$ = 2.26 min; m/z = 321 |
| 47 | $t_r$ = 1.42 min; m/z = 225 |
| 48 | m.p. = 163° C.; $t_r$ = 1.71 min; m/z = 285 |
| 49 | $t_r$ = 0.67 min; m/z = 207 |
| 50 | $t_r$ = 1.97 min; m/z = 275 |
| 51 | $t_r$ = 2.01 min; m/z = 275 |
| 52 | $t_r$ = 1.85 min; m/z = 255 |
| 53 | $t_r$ = 1.97 min; m/z = 276 |
| 54 | $t_r$ = 2.08 min; m/z = 301 |
| 55 | $t_r$ = 1.85 min; m/z = 275 |
| 56 | $t_r$ = 1.09 min; m/z = 208 |
| 57 | $t_r$ = 1.56 min; m/z = 242 |
| 58 | $t_r$ = 1.69 min; m/z = 286 |
| 59 | $t_r$ = 1.60 min; m/z = 257 |
| 60 | m.p. = 155° C.; $t_r$ = 1.80 min; m/z = 255 |
| 61 | $t_r$ = 1.98 min; m/z = 255 |
| 62 | $t_r$ = 2.27 min; m/z = 289 |
| 63 | $t_r$ = 2.35 min; m/z = 289 |
| 64 | $t_r$ = 2.09 min; m/z = 269 |
| 65 | $t_r$ = 2.53 min; m/z = 303 |
| 66 | $t_r$ = 2.59; 2.86 min; m/z = 333 |
| 67 | $t_r$ = 2.03 min; m/z = 273 |
| 68 | $t_r$ = 2.41 min; m/z = 299 |
| 69 | $t_r$ = 2.58; 2.64 min; m/z = 301 |
| 70 | $t_r$ = 2.26; 2.33 min; m/z = 301 |
| 71 | $t_r$ = 2.34 min; m/z = 299 |
| 72 | $t_r$ = 1.55 min; m/z = 229 |
| 73 | $t_r$ = 1.78 min; m/z = 257 |
| 74 | $t_r$ = 2.02 min; m/z = 283 |
| 75 | $t_r$ = 2.17 min; m/z = 285 |
| 76 | $t_r$ = 2.08; 2.17 min; m/z = 285 |
| 77 | $t_r$ = 2.14 min; m/z = 283 |
| 78 | $t_r$ = 1.34 min; m/z = 213 |
| 79 | $t_r$ = 2.46 min; m/z = 307 |
| 80 | $t_r$ = 2.23 min; m/z = 285 |
| 81 | $t_r$ = 1.72 min; m/z = 231 |
| 82 | $t_r$ = 2.30 min; m/z = 285 |
| 83 | $t_r$ = 2.22 min; m/z = 299 |
| 84 | $t_r$ = 2.10 min; m/z = 272 |
| 85 | $t_r$ = 2.42 min; m/z = 293 |
| 86 | $t_r$ = 2.06 min; m/z = 265 |
| 87 | $t_r$ = 2.64 min; m/z = 312 |
| 88 | $t_r$ = 2.42 min; m/z = 299 |
| 89 | $t_r$ = 2.54 min; m/z = 319 |
| 90 | $t_r$ = 1.70 min; m/z = 245 |
| 91 | $t_r$ = 2.00 min; m/z = 259 |
| 92 | $t_r$ = 2.20 min; m/z = 273 |
| 93 | $t_r$ = 2.76 min; m/z = 333 |
| 94 | $t_r$ = 2.34 min; m/z = 286 |
| 95 | $t_r$ = 2.22 min; m/z = 299 |
| 96 | $t_r$ = 2.04 min; m/z = 265 |
| 97 | $t_r$ = 2.26 min; m/z = 279 |

Synthesis Examples

Synthesis Example S.1:

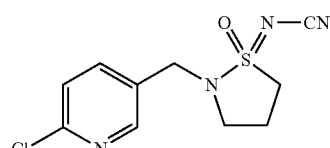

Compound no. 1

Step 1.1:

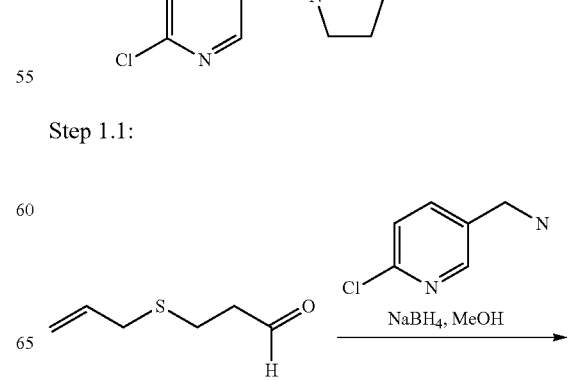

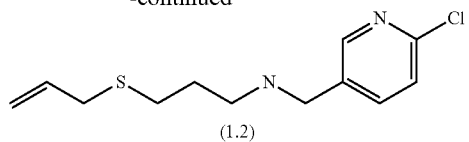

(1.2)

A solution of 3-allylsulfanyl-propionaldehyde (1.5 g, 11.8 mmol) in MeOH (15 mL) was added to a solution of C-(6-chloro-pyridin-3-yl)-methylamine (1.8 g, 12.6 mmol) in MeOH (15 mL) at 0° C. The resulting solution was stirred at this temperature for 1 h, then sodium borohydride (960 mg, 25.3 mmol) was added portionwise and stirring was continued for 16 h at room temperature. Volatiles were removed under reduced pressure and the residue was redissolved in $CH_2Cl_2$ and washed with saturated aqueous $NaHCO_3$ solution. The organic phase was dried over $MgSO_4$ and evaporated. Flash column chromatography purification ($NH_2$-modified $SiO_2$, gradient of cyclohexane/EtOAc) of the residue yielded 950 mg (31%) of allyl sulfide (1.2).

$^1$H-NMR: δ 8.31 (d, J=2.7 Hz, 1 H), 7.66 (dd, J=8.2, 2.7 Hz, 1 H), 7.28 (d, J=8.2 Hz, 1 H), 5.76 (m, 1 H), 5.08 (m, 2 H), 3.77 (s, 2 H), 3.11 (d, J=7.1 Hz, 2 H), 2.70 (t, J=7.1 Hz, 2 H), 2.51 (t, J=7.1 Hz, 2 H), 1.75 (q, J=7.1 Hz, 2 H) ppm.

Step 1.2:

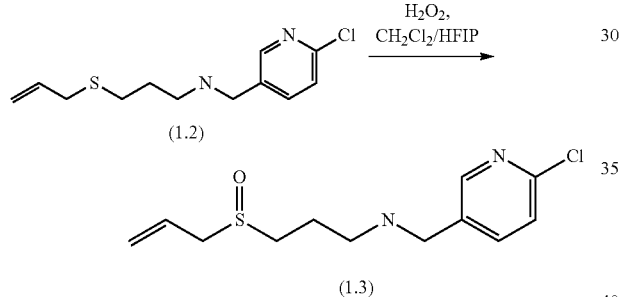

Hydrogen peroxide (1.51 mL of a 30% aqueous solution, 14.8 mmol) was added to a solution of the allyl sulfide (1.2) (950 mg, 3.7 mmol) in $CH_2Cl_2$/hexafluoroisopropanol (1:2, 12 mL) at 0° C., and the solution was stirred at room temperature for 4 h. After cooling to 0° C., saturated aqueous solutions of $Na_2SO_3$ and $NaHCO_3$ were added. The aqueous phase was extracted twice with $CH_2Cl_2$ and the combined organic phases were dried over $MgSO_4$ and evaporated.

The residue was purified by flash column chromatography ($NH_2$-modified $SiO_2$, gradient of cyclohexane/EtOAc) to give 950 mg (94%) of allyl sulfoxide (1.3).

$^1$H-NMR δ 8.30 (d, J=2.5 Hz, 2 H), 7.63 (dd, J=8.2, 2.5 Hz, 2 H), 8.27 (d, J=8.2 Hz, 2 H), 5.85 (m, 1 H), 5.39 (m, 2 H), 3.77 (s, 2 H), 3.45 (m, 2 H), 2.75 (m, 2 H), 2.51 (t, J=7.1 Hz, 2 H), 1.95 (q, J=6.6 Hz, 2 H) ppm.

Step 1.3:

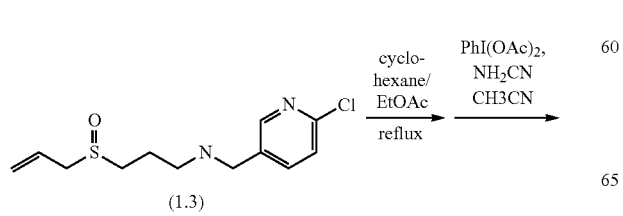

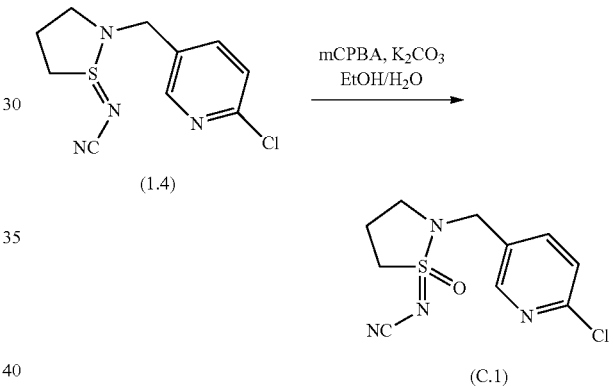

(1.4)

A solution of the allyl sulfoxide (1.3) (500 mg, 1.83 mmol) in cyclohexane/EtOAc (25 mL, 1:4) was refluxed for 24 h. Volatiles were removed under reduced pressure, and the residue was redissolved in $CH_3CN$ (10 mL) and cooled to 0° C. At this temperature, cyanamide (42 mg, 5.5 mmol) and diacetoxyiodosobenzene (322 mg, 2.0 mmol) were added and stirring was continued for 5 min at 0° C. and an additional hour at room temperature. The solution was then diluted with EtOAc and washed with $H_2O$. The organic phase was dried over $MgSO_4$ and evaporated under reduced pressure.

The residue was purified by flash column chromatography ($NH_2$-modified $SiO_2$, gradient of cyclohexane/EtOAc) to yield 86 mg (18%) of sulfiliminamide (1.4).

LC-MS: mass calcd. for $C_{10}H_{12}ClN_4S$ $[M+H]^+$ 254.7. found 254.8. $t_R$=1.57 min.

Step 1.4:

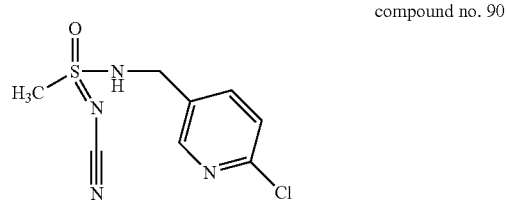

(C.1)

Meta-chloroperbenzoic acid (170 mg, 0.75 mmol) and $K_2CO_3$ (175 mg, 1.26 mmol) were added to a solution of the sulfiliminamide (1.4) (64 mg, 0.25 mmol) in EtOH/$H_2O$ (24:1, 5 mL). The solution was stirred at room temperature for 16 h, then diluted with $CH_2Cl_2$ and washed with saturated aqueous $NaHCO_3$-solution, dried over $MgSO_4$ and evaporated under reduced pressure.

The residue was purified by flash column chromatography ($NH_2$-modified $SiO_2$, gradient of cyclohexane/EtOAc) to yield 47 mg (54%) of sulfoximinamide (C.1).

LC-MS: mass calcd. for $C_{10}H_{12}ClN_4OS$ $[M+H]^+$ 270.7. found 270.8. $t_R$=1.77 min.

Synthesis Example S.2 compound no. 90

Step 2.1: Methanesulfinic acid (6-chloro-pyridin-3-yl methyl)-amide (2.2)

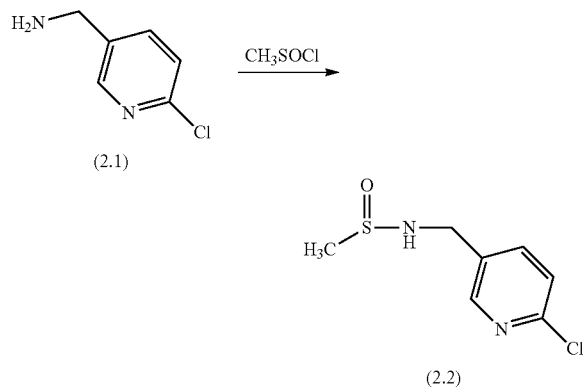

Methanesulfinyl chloride was obtained as described in the literature. A solution of C-(6-chloro-pyridin-3-yl)-methylamine (2.1) (25 g, 178 mmol) in tetrahydrofuran (200 ml) was cooled to 0° C. and methanesulfinyl chloride (7 g, 71 mmol) was added dropwise. The solution was allowed to warm to room temperature and stirred for 16 hours. The precipitate was removed by filtration, the filtrate was diluted with EtOAc and washed with H₂O. The organic phase was dried over Na₂SO₄ and evaporated under reduced pressure.

The residue was purified by flash column chromatography (gradient of cyclohexane/EtOAc) to yield 7.20 g of the Methanesulfinic acid (6-chloro-pyridin-3-ylmethyl)-amide (2.2).

LC-MS [M+H]⁺ 205.1. $t_R$=1.46 min

Step 2.1: N'-cyano, N-(6-chloro-pyridin-3-yl methyl) methanesulfonimidamide (C.2)

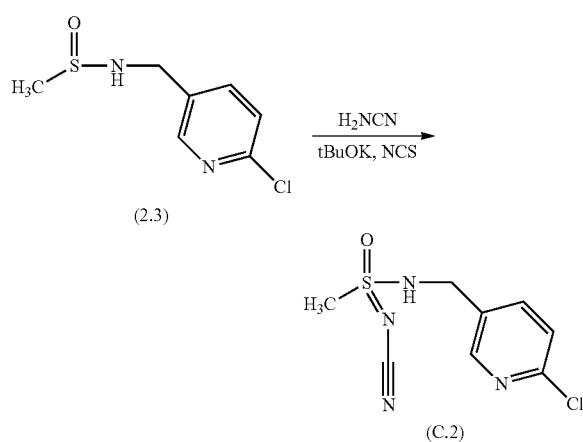

Cyanamide (88 mg, 2.1 mmol) and potassium tert. butoxide (225 mg, 2 mmol) were added to a solution of methanesulfinic acid (6-chloro-pyridin-3-yl methyl)-amide (2.3) (200 mg, 1 mmol) in dry acetonitrile. N-chlorosuccinimide (160 mg, 1.2 mmol) was added at room temperature and the solution was stirred for 3 hours.

The solvent was evaporated and the residue was purified by flash column chromatography (gradient EtOAc/MeOH) to yield 10 mg of the N'-cyano, N-(6-chloro-pyridin-3-yl methyl)methanesulfonimidamide (C.2)

LC-MS [M+H]⁺ 244.8, $t_R$=1.58 min.

Synthesis Example S.3

Compound no. 12

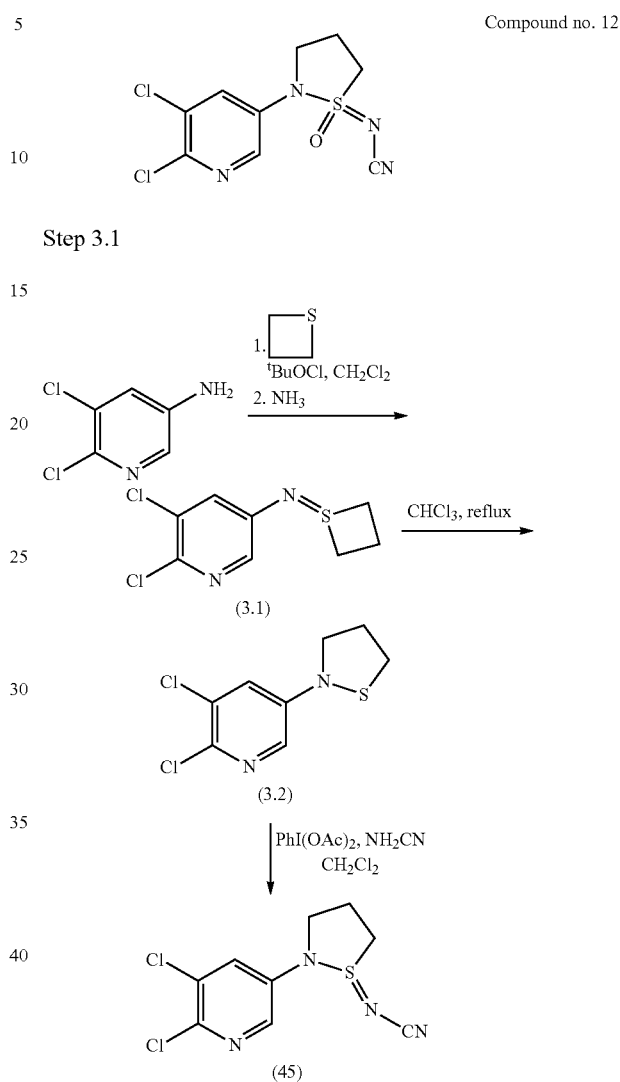

Step 3.1

A solution of ᵗBuOCl (0.65 g, 6.01 mmol) in CH₂Cl₂ (20 mL) was added dropwise to a solution of 3-amino-5,6-dichloropyridine (1 g, 6.01 mmol) and thietane (0.46 g, 6.01 mmol) in CH₂Cl₂ (35 mL) at −78° C. The resulting green suspension was stirred at −78° C. for 1 h, then an excess of NH₃ was condensed into the mixture. The suspension was then allowed to slowly warm to ambient temperature and concentrated to a volume of ca. 20 mL. The precipitate was removed by filtration and the filtrate was concentrated under reduced pressure to give 1.9 g of crude sulfilimine (3.1). The crude product was dissolved in CHCl₃ and the solution was refluxed for 3 h. Following evaporation of the solvent, the crude sulfenamide (3.2) was redissolved in CH₂Cl₂ (60 mL) and cooled to 0° C. At this temperature, cyanamide (0.32 g, 7.5 mmol) and diacetoxyiodosobenzene (2.4 g, 7.5 mmol) were added and the solution was stirred at 0° C. for 1 h, then allowed to warm to ambient temperature within 1 h. H₂O was added and the aqueous phase was extracted twice with CH₂Cl₂. The combined organic phases were washed with saturated aqueous NaCl-solution, dried over MgSO₄ and evaporated under reduced pressure. The residue was purified by flash column chromatography (NH$_2$-modified SiO$_2$, gradient of cyclohexane/EtOAc) to yield 0.5 g (30% overall) of sulfiliminamide (45).

LC-MS: mass calcd. for C$_9$H$_{10}$Cl$_2$N$_4$S [M+H]$^+$ 276. found 276; t$_R$=2.17 min.

Step 3.2

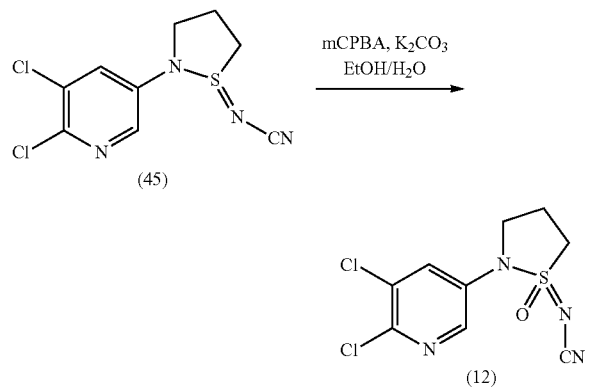

An aqueous solution of K$_2$CO$_3$ (1.15 g, 8.3 mmol) was added to a solution of sulfiliminamide (45) (380 mg, 1.38 mmol) in EtOH (6 mL), followed by dropwise addition of a solution of meta-chloroperbenzoic acid (360 mg, 2.1 mmol) in EtOH (2 mL). The solution was allowed to warm to ambient temperature and a solution of meta-chloroperbenzoic acid (360 mg, 2.1 mmol) in EtOH (2 mL) was added dropwise. The solution was stirred at room temperature for 30 min., then diluted with CH$_2$Cl$_2$ and washed with 10% aqueous Na$_2$CO$_3$-solution, dried over MgSO$_4$ and evaporated under reduced pressure. The residue was purified by flash column chromatography (NH$_2$-modified SiO$_2$, gradient of cyclohexane/EtOAc) to yield 360 mg (90%) of sulfoximinamide (12).

LC-MS: mass calcd. for C$_9$H$_{10}$Cl$_2$N4OS [M+H]$^+$ 292. found 292; t$_R$=2.45 min.

Synthesis Example 4

Compound no 3

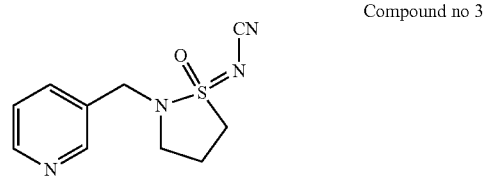

Step 4.1

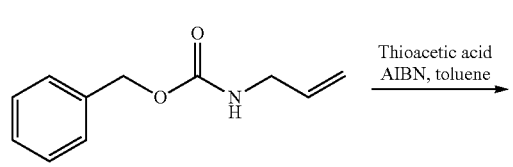

-continued

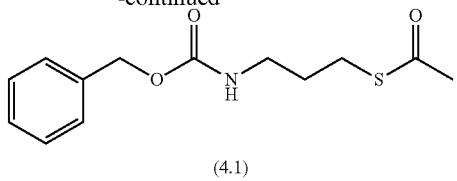

A solution of benzyl N-allylcarbamate (138.9 g, 0.69 mol), thioacetic acid (157.4 g, 2.07 mol) and AIBN (catalytic amount) in toluene (700 mL) was refluxed for 3 h. The solution was diluted with EtOAc and neutralized by slow addition of 10% aqueous Na$_2$CO$_3$-solution. The organic phase was washed with saturated aqueous NaCl-solution, dried over MgSO$_4$ and evaporated under reduced pressure to yield 181.6 g (98%) of thioacetate (4.1).

LC-MS: mass calcd. for C$_{13}$H$_{18}$NO$_3$S [M+H]$^+$ 268. found 268; t$_R$=2.80 min.

Step 4.2

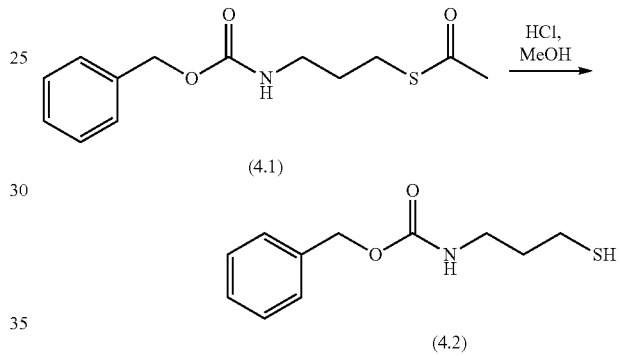

Concentrated HCl (65 mL) was added to a solution of thioacetate (4.1) (181.5 g, 0.68 mol) in MeOH (1 L) and the solution was refluxed for 16 h. The solvent was removed under reduced pressure and the residue was redissolved in methyl tert-butyl ether. The solution was neutralized by slow addition of 10% aqueous NaHCO$_3$-solution. The organic phase was dried over MgSO$_4$ and evaporated under reduced pressure to yield 124.2 g (81%) of thiol (4.2).

LC-MS: mass calcd. for C$_{11}$H$_{16}$NO$_2$S [M+H]$^+$ 226. found 226; t$_R$=2.89 min.

Step 4.3

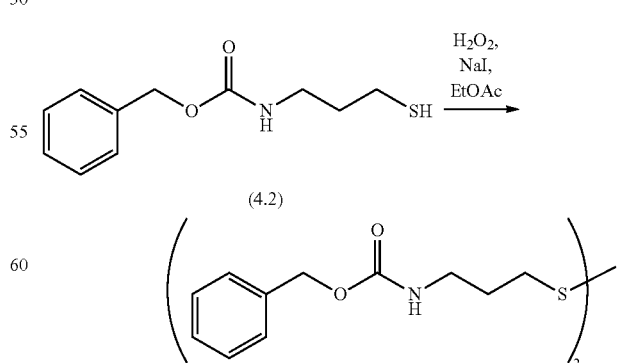

A solution of H₂O₂ (30% in H₂O, 62.4 g, 0.55 mol) was added dropwise to a solution of thiol (4.2) (124 g, 0.55 mol) and NaI (0.83 g, 5.5 mmol) in EtOAc (1 L) at 0° C. The solution was allowed to warm to ambient temperature and stirred for 1 h. Saturated aqueous Na₂S₂O₃-solution (300 mL) was added and the aqueous phase was extracted twice with EtOAc. The combined organic phases were washed with saturated aqueous NaCl-solution, dried over MgSO₄ and evaporated under reduced pressure. The residue was recrystallized from EtOAc to yield 92.4 g (75%) of disulfide (4.3).

LC-MS: mass calcd. for $C_{22}H_{29}N_2O_4S_2$ [M+H]⁺ 449. found 449; $t_R$=3.54 min.

Step 4.4

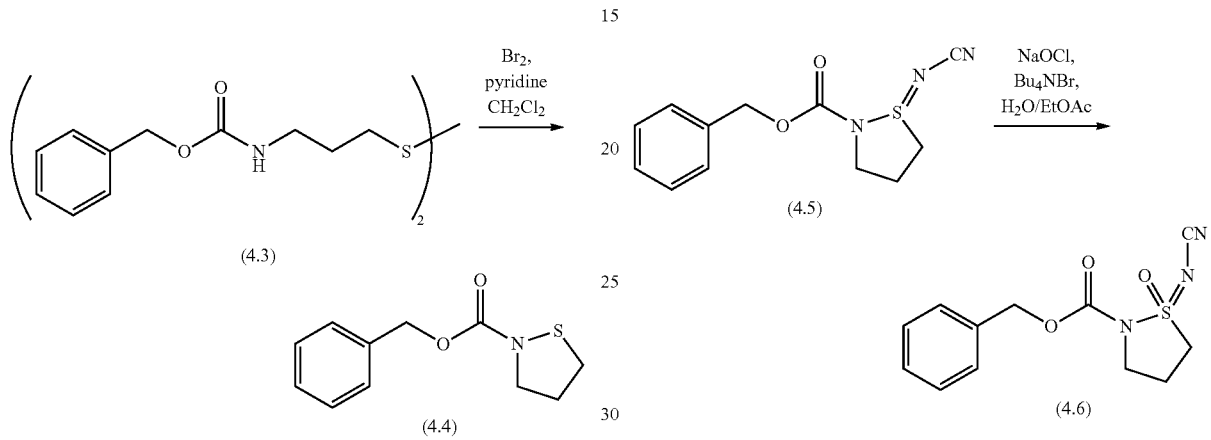

A solution of Br₂ (9.35 g, 58.5 mmol) in CH₂Cl₂ (100 mL) was added dropwise to a solution of disulfide (4.3) (25 g, 55.7 mmol) and pyridine (67 g, 0.85 mol) in CH₂Cl₂ (700 mL) at −78° C. within 4 h. The solution was allowed to warm to 0° C. and stirred at this temperature for 1 h. Saturated aqueous Na₂S₂O₃-solution (300 mL) was added and the aqueous phase was extracted with CH₂Cl₂. The combined organic phases were washed twice with H₂O, then with saturated aqueous NaCl-solution, dried over Na₂SO₄ and evaporated under reduced pressure to yield 25.6 g (97%) of sulfenamide (4.4) as a light brown oil.

LC-MS: mass calcd. for $C_{11}H_{14}NO_2S$ [M+H]⁺ 224. found 224; $t_R$=2.80 min.

Step 4.5

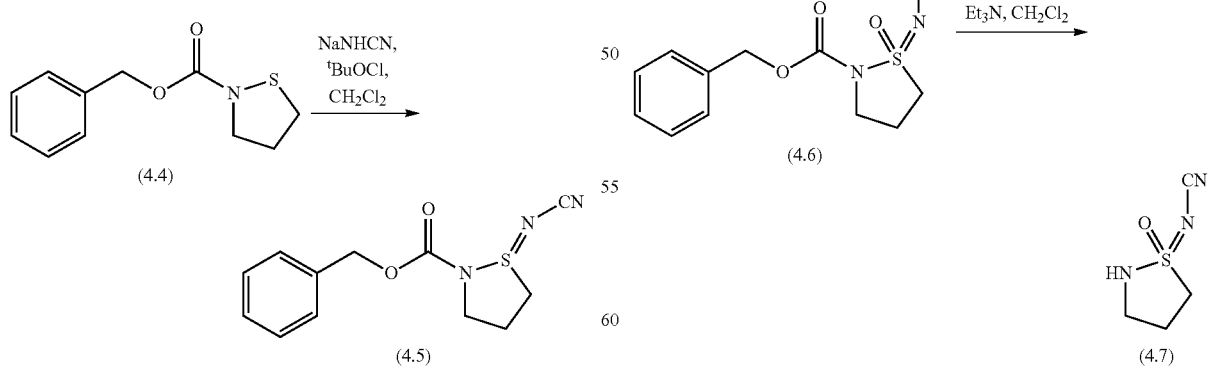

A solution of ᵗBuOCl (15 g, 138.1 mmol) in MeOH (240 mL) was added dropwise to a suspension of sodium cyanamide (8.84 g, 138.1 mmol) in MeOH (480 mL) at −50° C. A solution of sulfenamide (4.4) (25.7 g, 115.1 mmol) in MeOH (240 mL) was added dropwise to this solution at −50° C. within 25 min. The solution was stirred at this temperature for 1 h, then H₂O (600 mL) was added and stirring was continued at 10° C. for 1 h. The resulting suspension was filtered to yield a first crop (7.4 g) of the desired sulfiliminamide (4.5). The filtrate was concentrated to a volume of ca. 700 mL, and the resulting suspension was filtered. The residue was washed with H₂O and crystallized from MeOH to yield a second crop (7.4 g) of sulfiliminamide (4.5) (combined yield: 14.8 g, 46%).

LC-MS: mass calcd. for $C_{12}H_{14}N_3O_2S$ [M+H]⁺ 264. found 264; $t_R$=2.11 min.

Step 4.5

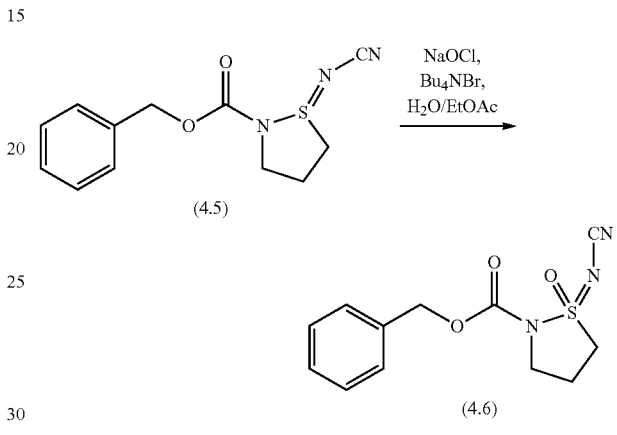

An aqueous solution of NaOCl (ca. 10%, 410 g) was added dropwise to a suspension of sulfiliminamide (4.5) (18.2 g, 69.1 mmol) and Bu₄NBr (0.9 g, 2.7 mmol) in EtOAc (450 mL). The biphasic solution was stirred at ambient temperature for 1 h, then the phases were separated and the aqueous phase was extracted with EtOAc. The combined organic phases were washed with H₂O, dried over Na₂SO₄ and evaporated under reduced pressure to yield 15.4 g (72%) of sulfoximinamide (4.6).

LC-MS: mass calcd. for $C_{12}H_{14}N_3O_3S$ [M+H]⁺ 280. found 280; $t_R$=2.29 min.

Step 4.6

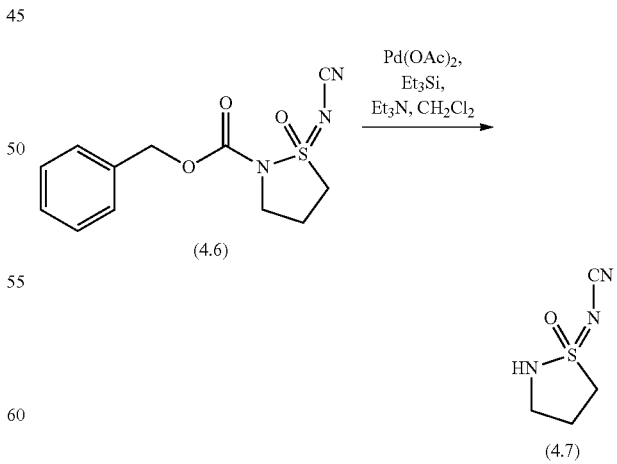

A solution of Et₃N (3.08 g, 30.4 mmol) in CH₂Cl₂ (60 mL) was added dropwise to a solution of Et₃Si (10.6 g, 91.3 mmol) and Pd(OAc)₂ (0.7 g, 3 mmol) in CH₂Cl₂ (120 mL). A solution of sulfoximinamide (4.6) (8.5 g, 30.4 mmol) in CH₂Cl₂

(60 mL) was added dropwise to the resulting dark solution. This solution was stirred at ambient temperature for 1 h, followed by concentration under reduced pressure. The residue was purified by flash column chromatography (SiO$_2$; CH$_2$Cl$_2$/MeOH 20:1) to give 2.6 g (59%) of sulfoximinamide (4.7).

LC-MS: mass calcd. for C$_4$H$_8$N$_3$OS [M+H]$^+$ 146. found 146; t$_R$=0.97 min.

Step 4.7

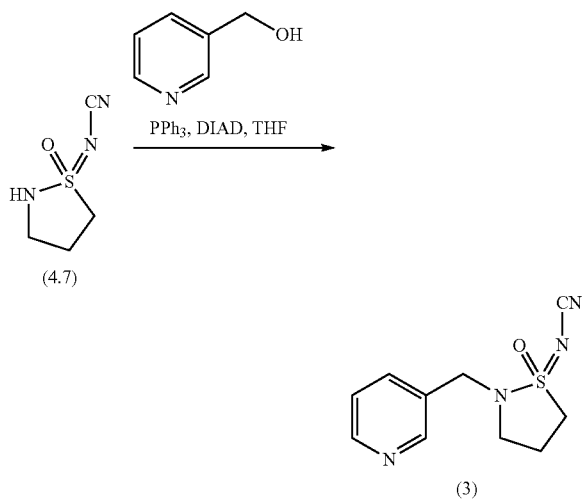

A solution of DIAD (0.3 g, 1.4 mmol) in THF (5 mL) was added dropwise to a suspension of polymer-bound PPh$_3$ (3.2 mmol/g, 1.4 mmol) in THF (15 mL) at 0° C., and the suspension was kept at this temperature for 15 min. A solution of 3-(hydroxymethyl)pyridine in THF (5 mL) was added dropwise, followed after 5 minutes by a solution of sulfoximinamide (4.7) (77 mg, 0.7 mmol) in THF (5 mL). The suspension was allowed to warm to ambient temperature and kept at this temperature for 16 h. The polymeric resin was removed by filtration and the filtrate was concentrated under reduced pressure. The residue was purified by flash column chromatography (SiO$_2$, CH$_2$Cl$_2$/MeOH 40:1) to yield 97 mg (56%) of the desired sulfoximinamide (3).

LC-MS: mass calcd. for C$_{10}$H$_{13}$N4OS [M+H]$^+$ 237. found 237; t$_R$=0.74 min.

B. Biological Examples of Action Against Pests

General Conditions

If not otherwise specified, most test solutions are prepared as follow:

The active compound is dissolved at the desired concentration in a mixture of 1:1 (vol:vol) distilled water:acteon. The test solutions are prepared at the day of use (and, if not otherwised specified, in general at concentrations wt/vol).

B.1 Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications. After application, microtiter plates were incubated at about 23±1° C. and about 50±5% relative humidity for 5 days. Egg and larval mortality was then visually assessed.

In this test, compound examples no. (given above in tables E.1, E.2 and E.3) 1, 4, 11, 14, 15, 16, 17, 18, 19, 29, 32, 39, 40, 44, 47, 48, 49, 52, 60, 84 and 85 at 2500 ppm showed over 75% mortality in comparison with untreated controls.

B.2 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compound examples no. (given above in tables E.1, E.2 and E.3) 1, 2, 4, 5, 7, 10, 11, 12, 13, 14, 15, 16, 17, 18, 19, 29, 32, 33, 39, 43, 60, 67, 73, 74, 75, 84, 85 and 90 at 2500 ppm showed over 75% mortality in comparison with untreated controls.

B.3a Green Peach Aphid (*Myzus persicae*) I

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compound examples no. (given above in tables E.1, E.2 and E.3) 1, 11, and 17 at 300 ppm showed over 75% mortality in comparison with untreated controls.

B.3b Green Peach Aphid (*Myzus persicae*) II

The active compounds were formulated in 50:50 acetone:water (vol:vol) and 100 ppm Kinetica™ surfactant.

Pepper plants in the 2$^{nd}$ leaf-pair stage (variety 'California Wonder') were infested with approximately 40 laboratory-reared aphids by placing infested leaf sections on top of the test plants. The leaf sections were removed after 24 hr. The leaves of the intact plants were dipped into gradient solutions of the test compound and allowed to dry. Test plants were maintained under fluorescent light (24 hour photoperiod) at about 25° C. and about 20-40% relative humidity. Aphid mortality on the treated plants, relative to mortality on check plants, was determined after 5 days.

In this test, compound examples no. (given above in tables E.1, E.2 and E.3) 1, 11, 12, 13, 14, 15, 17, 18, 19, 26, 29, 43, 60, 84, 85 and 90 at 300 ppm showed over 75% mortality in comparison with untreated controls.

B.4 Cowpea Aphid (*aphis craccivora*)

The active compound is dissolved at the desired concentration in a mixture of 1:1 (vol:vol) distilled water:acetone. The test solution is prepared at the day of use.

Potted cowpea plants colonized with approximately 100-150 aphids of various stages were sprayed after the pest population has been recorded. Population reduction was assessed after 24, 72, and 120 hours.

In this test, compound examples no. (given above in tables E.1, E.2 and E.3) 1, 2, 4, 5, 10, 11, 12, 13, 14, 15, 17, 18, 19, 29, 39, 43, 44, 48, 52, 60, 73, 84, 85, 86, 90 and 97 at 300 ppm showed over 75% mortality in comparison with untreated controls.

B.5 Cotton Aphid (*Aphis gossypii*) I

The active compounds were formulated in 50:50 (vol:vol) acetone:water and 100 ppm Kinetica™ surfactant.

Cotton plants at the cotyledon stage (one plant per pot) were infested by placing a heavily infested leaf from the main colony on top of each cotyledon. The aphids were allowed to transfer to the host plant overnight, and the leaf used to transfer the aphids was removed. The cotyledons were dipped in the test solution and allowed to dry. After 5 days, mortality counts were made.

In this test, compound examples no. (given above in tables E.1, E.2 and E.3) 1, 2, 11, 12, 14, 15, 17, 18, 26, 29, 60, 84, 85 and 90 at 300 ppm showed over 75% mortality in comparison with untreated controls.

B.6 Orchid Thrips (*dichromothrips corbetti*)

*Dichromothrips corbetti* adults used for bioassay were obtained from a colony maintained continuously under laboratory conditions. For testing purposes, the test compound was diluted to a concentration of 300 ppm (wt compound: vol diluent) in a 1:1 mixture of acetone:water (vol:vol), plus 0.01% vol/vol Kinetic® surfactant.

Thrips potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with 10-15 adult thrips. The petri dishes were then covered with lids. All test arenas were held under continuous light and a temperature of about 28° C. for duration of the assay. After 4 days, the numbers of live thrips were counted on each flower, and along inner walls of each petri dish. The level of thrips mortality was extrapolated from pre-treatment thrips numbers.

In this test, compound examples no. (given above in tables E.1, E.2 and E.3) 1, 2, 4, 11, 14, 15, 17, 18, 19, 29, 39, 60, 77 and 86 at 300 ppm showed over 75% mortality in comparison with untreated controls.

B.7 Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compound examples no. (given above in tables E.1, E.2 and E.3) 1, 5, 11, 12, 13, 14, 15, 17, 18, 19, 29, 39, 40, 60 and 84 at 300 ppm showed over 75% mortality in comparison with untreated controls.

We claim:

1. A sulfoximinamide compound of formula (I)

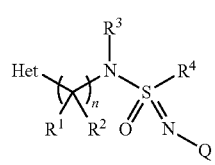

(I)

wherein

Q is $NO_2$ or CN;

n is 0, 1 or 2;

$R^1$, $R^2$ are selected independently from one another, and independently from n, from the group consisting of hydrogen, halogen, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, CN, $NO_2$, $C(O)R^c$, $C(O)OR^a$, $C(O)NR^aR^b$, $C(S)NR^aR^b$ and $S(O)_m R^c$, wherein the carbon atoms in the aforementioned groups may carry any combination of 1, 2 or 3 radicals $R^d$; or $R^1$ and $R^2$ form together with the carbon atom which they attached to a 3- to 6-membered carbocyclic ring, wherein the carbon atoms of the ring may carry any combination of 1 or 2 radicals $R^d$;

$R^3$ is selected from the group consisting of hydrogen, $C_1$-$C_6$-alkyl, $C_3$-$C_6$-cycloalkyl, $C_1$-$C_6$-alkoxy, $C_2$-$C_6$-alkenyl, $C_2$-$C_6$-alkynyl, $C(O)R^c$, $C(O)OR^a$, $C(O)NR^aR^b$, $C(S)NR^aR^b$, $SO_m R^c$ and $NR^e$, wherein the carbon atoms in the aforementioned groups may carry any combination of 1, 2 or 3 radicals $R^d$;

$R^4$ is selected from the group consisting of $C_1$-$C_6$-alkyl, $C_3$-$C_6$-cycloalkyl, $C_2$-$C_6$-alkenyl, $C_2$-$C_6$-alkynyl and $NR^eR^f$, wherein the carbon atoms in the aforementioned groups may carry any combination of 1, 2 or 3 radicals $R^d$; or $R^3$ and $R^4$ form, together with the nitrogen and sulfur atom they are bound to, a saturated or unsaturated 4-, 5- or 6-membered heterocyclic ring, optionally containing an additional heteroatom selected from the group consisting of N, O, and S, whereas the carbon atoms of the heterocyclic ring may optionally carry any combination of 1 or 2 radicals $R^d$ and whereas the additional N atom optionally may carry $R^e$;

Het is

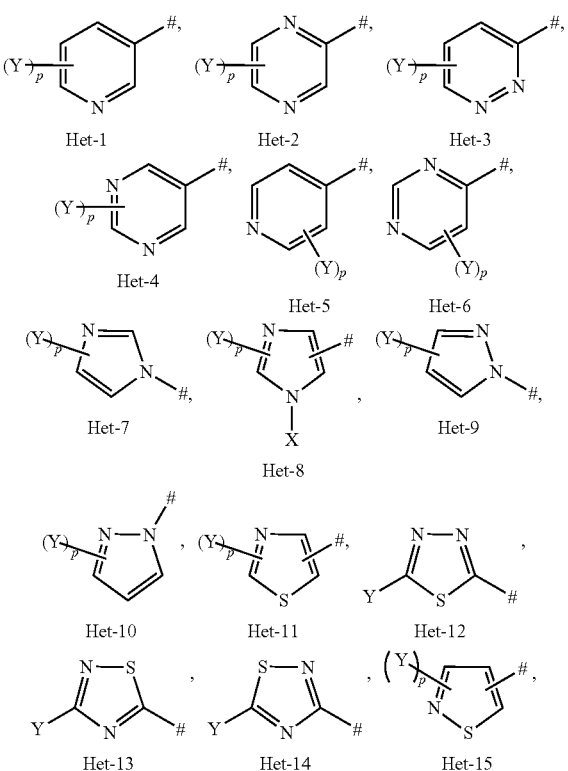

117

-continued

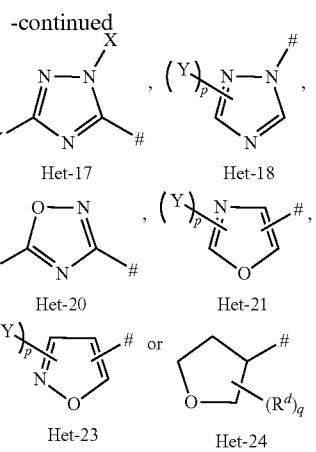

wherein # denotes the bond in formula (I), and
X is selected from the group consisting of hydrogen, $C_1$-$C_6$ alkyl, $C_1$-$C_6$ haloalkyl, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C(O)R^e$, $C(O)OR^5$, $C(O)NR^aR^b$, $C(S)NR^aR^b$ and $S(O)_m R^c$, wherein
the carbon atoms in the aforementioned groups may carry any combination of 1, 2 or 3 radicals $R^d$;
Y is selected from the group consisting of halogen, $C_1$-$C_6$ alkyl, $C_3$-$C_6$ cycloalkyl, $C_2$-$C_6$ alkenyl, $C_2$-$C_6$ alkynyl, $C_1$-$C_6$ alkoxy, CN, $NO_2$, $S(O)_m R^c$, $C(O)R^c$, $C(O)OR^a$, $C(O)NR^aR^b$ and $C(S)NR^aR^b$, wherein
the carbon atoms in the aforementioned groups may carry any combination of 1, 2 or 3 radicals $R^d$;
p is 0, 1 or 2;
q is 0, 1, or 2;
and wherein
$R^a$, $R^b$ are selected independently from one another from the group consisting of hydrogen, $C_1$-$C_4$-alkyl, $C_1$-$C_4$-haloalkyl, $C_3$-$C_6$-cycloalkyl, $C_3$-$C_6$-alkenyl, $C_3$-$C_6$-haloalkenyl and $C_3$-$C_6$-alkynyl;
$R^c$ is selected from the group consisting of $C_1$-$C_4$-alkyl, $C_1$-$C_4$-haloalkyl, $C_3$-$C_6$-cycloalkyl, $C_2$-$C_6$-alkenyl, $C_2$-$C_6$-haloalkenyl and $C_2$-$C_6$-alkynyl;
$R^d$ is selected from the group consisting of halogen, $C_1$-$C_4$-alkyl, $C_1$-$C_4$-haloalkyl, $C_3$-$C_6$-cycloalkyl, $C_2$-$C_6$-alkenyl, $C_2$-$C_6$-haloalkenyl or $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;
$R^e$, $R^f$ are selected independently from one another from the group consisting of hydrogen, $C_1$-$C_4$-alkyl, $C_1$-$C_4$-haloalkyl, $C_3$-$C_6$-cycloalkyl, $C_3$-$C_6$-alkenyl, $C_3$-$C_6$-haloalkenyl, $C_3$-$C_6$-alkynyl, $C(O)R^c$, $C(O)OR^a$, $C(O)NR^aR^b$ and $C(S)NR^aR^b$;
m is 0, 1 or 2;
or its agriculturally or veterinarily acceptable salt, enantiomer or diastereomer.

2. The sulfoximinamide compound of formula (I) as claimed in claim 1, wherein
Het is

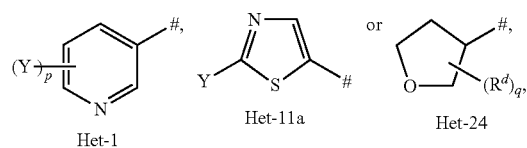

118 and wherein
Y is selected from the group consisting of halogen, $C_1$-$C_4$-haloalkyl and $C_1$-$C_4$-alkyl;
p is 0, 1 or 2;
$R^d$ is selected from the group consisting of halogen, $C_1$-$C_4$-alkyl, $C_1$-$C_4$-haloalkyl, $C_3$-$C_6$-cycloalkyl, $C_2$-$C_6$-alkenyl, $C_2$-$C_6$-haloalkenyl or $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio; and
q is 0, 1, or 2.

3. The sulfoximinamide compound of formula (I) as defined in claim 1, wherein
Q is CN.

4. The sulfoximinamide compound of formula (I) as defined in claim 1, wherein
n is 0.

5. The sulfoximinamide compound of formula (I) as defined in claim 1, wherein
n is 1
$R^1$, $R^2$ are, independently from one another and independently from n, selected from the group consisting of hydrogen, $C_1$-$C_4$-alkyl, $C_1$-$C_4$-haloalkyl and $C_3$-$C_6$-cycloalkyl.

6. The sulfoximinamide compound of formula (I) as defined in claim 1, wherein
$R^3$ is selected from the group consisting of hydrogen, $C_1$-$C_6$-alkyl, $C_3$-$C_6$-cycloalkyl, $C_1$-$C_6$-haloalkyl and $C_4$-$C_6$-cycloalkylalkyl.

7. The sulfoximinamide compound of formula (I) as defined in claim 1, wherein
$R^3$ is selected from the group consisting of hydrogen, methyl, ethyl, propyl, isopropyl, cyclopropyl, tert-butyl and cyclopropylmethyl.

8. The sulfoximinamide compound of formula (I) as defined in claim 1, wherein
$R^4$ is methyl or ethyl.

9. The sulfoximinamide compound of formula (I) as defined in claim 1, wherein
$R^3$ and $R^4$ form, together with the nitrogen and sulfur atom they are bound to, a saturated or unsaturated 5- or 6-membered heterocyclic ring, whereas the carbon atoms of the heterocyclic ring may optionally carry any combination of 1 or 2 radicals $R^d$, and wherein
$R^d$ is selected from the group consisting of halogen, $C_1$-$C_4$-alkyl, $C_1$-$C_4$-haloalkyl, $C_3$-$C_6$-cycloalkyl, $C_2$-$C_6$-alkenyl, $C_2$-$C_6$-haloalkenyl or $C_2$-$C_6$-alkynyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio.

10. The sulfoximinamide compound of formula (I) as defined in claim 1, wherein
Het is

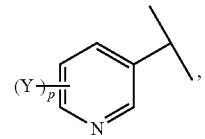

wherein
Y is selected from the group consisting of halogen, $C_1$-$C_4$-haloalkyl and $C_1$-$C_4$-alkyl, and
p is 0, 1 or 2;
Q is CN;
n is 0 or 1;
$R^1$, $R^2$ are independently from one another selected from the group consisting of hydrogen, methyl, ethyl and trifluoromethyl, or $R^1$ and $R^2$ form cyclopropane together with the carbon atom to which they are attached;

$R^3$ is selected from the group consisting of hydrogen, methyl, ethyl, propyl, isopropyl, cyclopropyl, tert-butyl and cyclopropylmethyl;

$R^4$ is methyl or ethyl; or $R^3$ and $R^4$ form, together with the nitrogen and sulfur atom they are bound to, a saturated 4-, 5- or 6-membered heterocyclic ring.

11. The sulfoximinamide compound of formula (I) as defined in claim 1, wherein

Het is

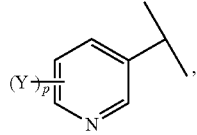

wherein

Y is selected from the group consisting of halogen and $C_1$-$C_4$-haloalkyl;

p is 1;

Q is CN;

n is 0;

$R^3$ is selected from the group consisting of hydrogen, methyl, ethyl, propyl, isopropyl, cyclopropyl, tert-butyl and cyclopropylmethyl;

$R^4$ is methyl or ethyl; or $R^3$ and $R^4$ form, together with the nitrogen and sulfur atom they are bound to, a saturated 4-, 5- or 6-membered heterocyclic ring.

12. The sulfoximinamide compound of formula (I) as defined in claim 1, wherein

Het is

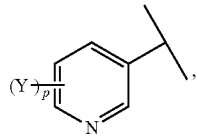

wherein

Y is selected from the group consisting of halogen and $C_1$-$C_4$-haloalkyl;

p is 1;

Q is CN;

n is 0;

$R^3$ and $R^4$ form, together with the nitrogen and sulfur atom they are bound to, an unsubstituted isothiazolidine or an unsubstituted [1,2] thiazinane ring.

13. A compound of formula (II)

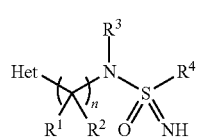

(II)

wherein n, Het, $R^1$, $R^2$, $R^3$ and $R^4$ are defined as in claim 1.

14. A compound of formula (VII)

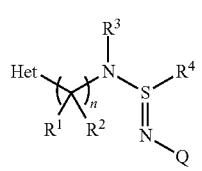

(VII)

wherein n, Het, $R^1$, $R^2$, $R^3$, $R^4$ and Q are defined as in claim 1.

15. A compound of formula (IV)

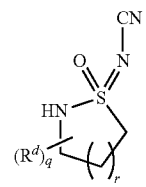

(IV)

wherein r is 1 or 2;

q is 0, 1 or 2;

and $R^d$ is defined as in claim 1.

16. A composition comprising at least one sulfoximinamide compound of the formula I as defined in claim 1, or the enantiomer, diastereomer or salt thereof and at least one inert liquid and/or solid carrier.

17. An agricultural or veterinary composition for combating animal pests comprising a pesticidal effective amount of at least one sulfoximinamide compound of the formula I as defined in claim 1, or the enantiomer, diastereomer or agriculturally or veterinary useful salt thereof, and at least one inert liquid and/or solid acceptable carrier and, optionally, a surfactant.

18. A method for combating or controlling insects, arachnids or nematodes comprising contacting an insect, arachnid or nematode or their food supply, habitat or breeding grounds with a pesticidally effective amount of at least one sulfoximinamide compound of the formula I as defined in claim 1, or the enantiomers, diastereomers or salts thereof or a composition comprising at least such one compound of formula I.

19. A method for protecting growing plants from attack or infestation by insects, arachnids or nematodes comprising contacting a plant, or soil or water in which the plant is growing, with a pesticidally effective amount of at least one sulfoximinamide compound of the formula I as defined in claim 1, or the enantiomers, diastereomers or salts thereof or a composition comprising at least such one compound of formula I.

20. The method of claim 18, wherein the animal pest is from the order Hemiptera or Thysanoptera.

21. A method for the protection of seeds from soil insects and of the seedlings' roots and shoots from soil and foliar insects comprising contacting the seeds before sowing and/or after pregermination with at least one sulfoximinamide compound of the formula I as defined in claim 1, or the enantiomers, diastereomers or salts thereof or a composition comprising at least such compound.

22. The method of claim 21, wherein the sulfoximinamide compound of the formula I is applied in an amount of from 100 mg to 10 kg per 100 kg of seeds.

23. The method of claim 21, wherein of the resulting plant's roots and shoots are protected.

24. A seed treated with a sulfoximinamide compound of the formula I as defined in claim 1, or the enatiomers, diastereomers or salts thereof, in an amount of from 0.1 g to 10 kg per 100 kg of seed.

* * * * *